(12) United States Patent
Kishi

(10) Patent No.: US 9,851,782 B2
(45) Date of Patent: Dec. 26, 2017

(54) OPERATION SUPPORT DEVICE AND ATTACHMENT AND DETACHMENT METHOD THEREOF

(71) Applicant: OLYMPUS CORPORATION, Tokyo (JP)

(72) Inventor: Kosuke Kishi, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 132 days.

(21) Appl. No.: 14/168,496

(22) Filed: Jan. 30, 2014

(65) Prior Publication Data

US 2014/0144258 A1 May 29, 2014

Related U.S. Application Data

(63) Continuation of application No. PCT/JP2012/070415, filed on Aug. 3, 2012.
(Continued)

(30) Foreign Application Priority Data

Feb. 6, 2012 (JP) ................... 2012-023443

(51) Int. Cl.
*A61B 17/00* (2006.01)
*G06F 3/01* (2006.01)
(Continued)

(52) U.S. Cl.
CPC ............... *G06F 3/01* (2013.01); *A61B 17/29* (2013.01); *A61B 17/32002* (2013.01);
(Continued)

(58) Field of Classification Search
CPC .................................. A61B 17/28; A61B 17/29
See application file for complete search history.

(56) References Cited

U.S. PATENT DOCUMENTS 3,139,990 A 7/1964 Jelatis et al.
3,923,166 A 12/1975 Fletcher et al.
(Continued)

FOREIGN PATENT DOCUMENTS

CN 101027010 A 8/2007
CN 101167658 A 4/2008
(Continued)

OTHER PUBLICATIONS

U.S. Office Action dated Apr. 9, 2015 received in related U.S. Appl. No. 14/169,675.
(Continued)

*Primary Examiner* — Melanie Tyson
(74) *Attorney, Agent, or Firm* — Scully, Scott, Murphy & Presser, P.C.

(57) ABSTRACT

An operation support device includes a connecting body in which a first support body and a second support body are detachably connected to each other; a first shaft engaging section; a shaft connecting member having a connection engaging section engaged with the first shaft engaging section; and a shaft fixing member. The shaft fixing member is movably installed with respect to a first shaft section or a second shaft section and is configured to selectively form a shaft engagement fixing state in which the connection engaging section is held down to retain an engagement state such that the connection engaging section is engaged with the first shaft engaging section and a second state in which holding down to the connection engaging section is released in accordance with a moved position with a moved position of the shaft fixing member.

6 Claims, 26 Drawing Sheets

Related U.S. Application Data

(60) Provisional application No. 61/515,203, filed on Aug. 4, 2011.

(51) Int. Cl.

| | | |
|---|---|---|
| *A61B 17/29* | (2006.01) | |
| *A61B 17/32* | (2006.01) | |
| *A61B 18/14* | (2006.01) | |
| *B25J 13/02* | (2006.01) | |
| *A61B 34/30* | (2016.01) | |
| *A61B 46/10* | (2016.01) | |
| *A61B 17/068* | (2006.01) | |
| *A61B 46/23* | (2016.01) | |
| *A61B 90/00* | (2016.01) | |

(52) U.S. Cl.
CPC .......... *A61B 18/1402* (2013.01); *A61B 34/30* (2016.02); *A61B 46/10* (2016.02); *B25J 13/02* (2013.01); *A61B 17/068* (2013.01); *A61B 46/23* (2016.02); *A61B 2017/00119* (2013.01); *A61B 2017/00477* (2013.01); *A61B 2017/00482* (2013.01); *A61B 2090/0813* (2016.02); *Y10S 901/08* (2013.01); *Y10S 901/09* (2013.01); *Y10S 901/30* (2013.01); *Y10T 29/49826* (2015.01); *Y10T 74/18056* (2015.01)

(56) References Cited

U.S. PATENT DOCUMENTS

| | | | |
|---|---|---|---|
| 4,672,281 A | | 6/1987 | Yagusic et al. |
| 4,830,569 A | | 5/1989 | Jannborg |
| 4,872,803 A | | 10/1989 | Asakawa |
| 5,214,969 A | | 6/1993 | Adkins et al. |
| 5,603,723 A | | 2/1997 | Aranyi et al. |
| 5,632,432 A | | 5/1997 | Schulze et al. |
| 5,649,956 A | | 7/1997 | Jensen et al. |
| 5,656,903 A | | 8/1997 | Shui et al. |
| 5,712,543 A | | 1/1998 | Sjostrom |
| 5,760,530 A | | 6/1998 | Kolesar |
| 5,762,458 A | | 6/1998 | Wang et al. |
| 5,784,542 A | | 7/1998 | Ohm et al. |
| 5,817,119 A | | 10/1998 | Klieman et al. |
| 5,836,869 A | | 11/1998 | Kudo et al. |
| 5,855,583 A | | 1/1999 | Wang et al. |
| 5,871,493 A | | 2/1999 | Sjostrom et al. |
| 5,876,325 A | | 3/1999 | Mizuno et al. |
| 6,007,550 A | | 12/1999 | Wang et al. |
| 6,039,748 A | * | 3/2000 | Savage ............ A61B 17/32002 606/107 |
| 6,063,095 A | | 5/2000 | Wang et al. |
| 6,082,797 A | | 7/2000 | Antonette |
| 6,090,122 A | | 7/2000 | Sjostrom et al. |
| 6,102,850 A | | 8/2000 | Wang et al. |
| 6,132,368 A | | 10/2000 | Cooper |
| 6,132,441 A | | 10/2000 | Grace |
| 6,206,903 B1 | | 3/2001 | Ramans |
| 6,246,200 B1 | | 6/2001 | Blumenkranz et al. |
| 6,328,752 B1 | | 12/2001 | Sjostrom et al. |
| 6,346,072 B1 | | 2/2002 | Cooper |
| 6,430,473 B1 | | 8/2002 | Lee et al. |
| 6,436,107 B1 | | 8/2002 | Wang et al. |
| 6,441,577 B2 | | 8/2002 | Blumenkranz et al. |
| 6,557,558 B1 | | 5/2003 | Tajima et al. |
| 6,574,355 B2 | | 6/2003 | Green |
| 6,587,750 B2 | | 7/2003 | Gerbi et al. |
| 6,602,185 B1 | | 8/2003 | Uchikubo |
| 6,645,196 B1 | | 11/2003 | Nixon et al. |
| 6,666,876 B2 | | 12/2003 | Kawai et al. |
| 6,676,684 B1 | | 1/2004 | Morley et al. |
| 6,685,698 B2 | | 2/2004 | Morley et al. |
| 6,699,177 B1 | | 3/2004 | Wang et al. |
| 6,746,443 B1 | | 6/2004 | Morley et al. |
| 6,783,524 B2 | 8/2004 | Anderson et al. |
| 6,786,896 B1 | 9/2004 | Madhani et al. |
| 6,853,879 B2 | 2/2005 | Sunaoshi |
| 6,866,671 B2 | 3/2005 | Tierney et al. |
| 6,905,460 B2 | 6/2005 | Wang et al. |
| 6,913,613 B2 | 7/2005 | Schwarz et al. |
| 7,083,571 B2 | 8/2006 | Wang et al. |
| 7,101,363 B2 | 9/2006 | Nishizawa et al. |
| 7,107,124 B2 | 9/2006 | Green |
| 7,118,582 B1 | 10/2006 | Wang et al. |
| 7,273,488 B2 | 9/2007 | Nakamura et al. |
| 7,295,893 B2 | 11/2007 | Sunaoshi |
| 7,313,464 B1 | 12/2007 | Perreault et al. |
| 7,331,967 B2 | 2/2008 | Lee et al. |
| 7,357,774 B2 | 4/2008 | Cooper |
| 7,373,219 B2 | 5/2008 | Nowlin et al. |
| 7,422,592 B2 | 9/2008 | Morley et al. |
| 7,476,237 B2 | 1/2009 | Taniguchi et al. |
| 7,549,998 B2 | 6/2009 | Braun |
| 7,594,912 B2 | 9/2009 | Cooper et al. |
| 7,608,083 B2 | 10/2009 | Lee et al. |
| 7,654,431 B2 | 2/2010 | Hueil et al. |
| 7,666,191 B2 | 2/2010 | Orban, III et al. |
| 7,674,255 B2 | 3/2010 | Braun |
| 7,695,481 B2 | 4/2010 | Wang et al. |
| 7,699,835 B2 | 4/2010 | Lee et al. |
| 7,699,855 B2 | 4/2010 | Anderson et al. |
| 7,778,733 B2 | 8/2010 | Nowlin et al. |
| 7,819,884 B2 | 10/2010 | Lee et al. |
| 7,819,885 B2 | 10/2010 | Cooper |
| 7,862,579 B2 | 1/2011 | Ortiz et al. |
| 7,865,266 B2 | 1/2011 | Moll et al. |
| 7,955,321 B2 | 6/2011 | Kishi et al. |
| 8,105,320 B2 | 1/2012 | Manzo |
| 8,155,479 B2 | 4/2012 | Hoffman et al. |
| 8,267,958 B2 | 9/2012 | Braun |
| 8,350,806 B2 | 1/2013 | Nagasaka et al. |
| 8,423,186 B2 | 4/2013 | Itkowitz et al. |
| 8,460,277 B2 | 6/2013 | Suarez et al. |
| 8,496,647 B2 | 7/2013 | Blumenkranz et al. |
| 8,540,748 B2 | 9/2013 | Murphy et al. |
| 8,744,137 B2 | 6/2014 | Sakai et al. |
| 8,845,681 B2 | 9/2014 | Grace |
| 8,876,858 B2 | 11/2014 | Braun |
| 8,888,789 B2 | 11/2014 | Prisco et al. |
| 8,903,549 B2 | 12/2014 | Itkowitz et al. |
| 8,906,002 B2 | 12/2014 | Kishi et al. |
| 9,039,681 B2 | 5/2015 | Wang et al. |
| 9,283,675 B2 | 3/2016 | Hager et al. |
| 9,308,009 B2 | 4/2016 | Madan et al. |
| 9,308,646 B2 | 4/2016 | Lim et al. |
| 2001/0021859 A1 | 9/2001 | Kawai et al. |
| 2001/0055062 A1 | 12/2001 | Shioda et al. |
| 2002/0072736 A1 | 6/2002 | Tierney et al. |
| 2002/0091374 A1 | 7/2002 | Cooper |
| 2002/0128552 A1 | 9/2002 | Nowlin et al. |
| 2003/0033204 A1 | 2/2003 | Sunaoshi |
| 2003/0060927 A1 | 3/2003 | Gerbi et al. |
| 2003/0069471 A1 | 4/2003 | Nakanishi et al. |
| 2003/0083648 A1 | 5/2003 | Wang et al. |
| 2003/0100817 A1 | 5/2003 | Wang et al. |
| 2003/0216723 A1 | 11/2003 | Shinmura et al. |
| 2004/0049205 A1 | 3/2004 | Lee et al. |
| 2004/0092912 A1 | 5/2004 | Jinno et al. |
| 2004/0111113 A1 | 6/2004 | Nakamura et al. |
| 2004/0140787 A1 | 7/2004 | Okamoto et al. |
| 2004/0186345 A1 | 9/2004 | Yang et al. |
| 2004/0186624 A1 | 9/2004 | Oda et al. |
| 2004/0243147 A1 | 12/2004 | Lipow |
| 2004/0246469 A1 | 12/2004 | Hirose |
| 2005/0020876 A1 | 1/2005 | Shioda et al. |
| 2005/0021050 A1 | 1/2005 | Cooper |
| 2005/0033117 A1 | 2/2005 | Ozaki et al. |
| 2005/0125027 A1 | 6/2005 | Knodel et al. |
| 2005/0149003 A1 | 7/2005 | Tierney et al. |
| 2005/0228365 A1 | 10/2005 | Wang et al. |
| 2005/0273086 A1 | 12/2005 | Green et al. |
| 2006/0052664 A1 | 3/2006 | Julian et al. |
| 2006/0074408 A1 | 4/2006 | Jinno et al. |

(56) References Cited

U.S. PATENT DOCUMENTS

| | | |
|---|---|---|
| 2006/0079865 A1 | 4/2006 | Jinno et al. |
| 2006/0079866 A1 | 4/2006 | Jinno et al. |
| 2006/0087746 A1 | 4/2006 | Lipow |
| 2006/0116973 A1 | 6/2006 | Okamoto et al. |
| 2006/0149162 A1 | 7/2006 | Daw et al. |
| 2006/0155262 A1 | 7/2006 | Kishi et al. |
| 2006/0161138 A1 | 7/2006 | Orban, III et al. |
| 2006/0190031 A1 | 8/2006 | Wales et al. |
| 2006/0235436 A1 | 10/2006 | Anderson et al. |
| 2007/0012135 A1 | 1/2007 | Tierney et al. |
| 2007/0089557 A1 | 4/2007 | Solomon et al. |
| 2007/0119274 A1 | 5/2007 | Devengenzo et al. |
| 2007/0137372 A1 | 6/2007 | Devengenzo et al. |
| 2007/0138992 A1 | 6/2007 | Prisco et al. |
| 2007/0142823 A1 | 6/2007 | Prisco et al. |
| 2007/0142825 A1 | 6/2007 | Prisco et al. |
| 2007/0156122 A1 | 7/2007 | Cooper |
| 2007/0167679 A1 | 7/2007 | Miyamoto et al. |
| 2007/0167680 A1 | 7/2007 | Miyamoto et al. |
| 2007/0173689 A1 | 7/2007 | Ozaki et al. |
| 2007/0197896 A1 | 8/2007 | Moll et al. |
| 2007/0208375 A1 | 9/2007 | Nishizawa et al. |
| 2007/0219668 A1 | 9/2007 | Takahashi et al. |
| 2007/0225550 A1 | 9/2007 | Gattani et al. |
| 2007/0249897 A1 | 10/2007 | Miyamoto et al. |
| 2007/0265638 A1 | 11/2007 | Lipow et al. |
| 2008/0015611 A1 | 1/2008 | Jinno et al. |
| 2008/0033240 A1 | 2/2008 | Hoffman et al. |
| 2008/0046122 A1 | 2/2008 | Manzo et al. |
| 2008/0051631 A1 | 2/2008 | Dejima et al. |
| 2008/0059131 A1 | 3/2008 | Tokita et al. |
| 2008/0103524 A1 | 5/2008 | Grace |
| 2008/0140088 A1 | 6/2008 | Orban, III |
| 2008/0147091 A1 | 6/2008 | Cooper |
| 2008/0177285 A1 | 7/2008 | Brock et al. |
| 2008/0204425 A1 | 8/2008 | Nagasaka et al. |
| 2008/0215065 A1 | 9/2008 | Wang et al. |
| 2008/0228196 A1 | 9/2008 | Wang et al. |
| 2008/0234866 A1 | 9/2008 | Kishi et al. |
| 2008/0243142 A1 | 10/2008 | Gildenberg |
| 2008/0262654 A1 | 10/2008 | Omori et al. |
| 2008/0287735 A1 | 11/2008 | Takemoto et al. |
| 2008/0312668 A1 | 12/2008 | Grace |
| 2009/0018700 A1 | 1/2009 | Okamoto et al. |
| 2009/0022262 A1 | 1/2009 | Ohishi |
| 2009/0030273 A1 | 1/2009 | Murakami |
| 2009/0034820 A1 | 2/2009 | Sugiyama |
| 2009/0036736 A1 | 2/2009 | Dejima et al. |
| 2009/0036902 A1 | 2/2009 | DiMaio et al. |
| 2009/0046146 A1 | 2/2009 | Hoyt |
| 2009/0057369 A1 | 3/2009 | Smith et al. |
| 2009/0088634 A1 | 4/2009 | Zhao et al. |
| 2009/0088773 A1 | 4/2009 | Zhao et al. |
| 2009/0088897 A1 | 4/2009 | Zhao et al. |
| 2009/0132088 A1 | 5/2009 | Taitler |
| 2009/0163948 A1 | 6/2009 | Sunaoshi et al. |
| 2009/0171147 A1 | 7/2009 | Lee et al. |
| 2009/0182193 A1 | 7/2009 | Whitman et al. |
| 2009/0193299 A1 | 7/2009 | Sekiguchi et al. |
| 2009/0204911 A1 | 8/2009 | Sekiguchi et al. |
| 2009/0247877 A1 | 10/2009 | Tanaka et al. |
| 2009/0281378 A1 | 11/2009 | Banju et al. |
| 2009/0326318 A1 | 12/2009 | Tagnaccini et al. |
| 2010/0010673 A1 | 1/2010 | Wang et al. |
| 2010/0013812 A1 | 1/2010 | Gu et al. |
| 2010/0087835 A1 | 4/2010 | Blumenkranz et al. |
| 2010/0160728 A1 | 6/2010 | Yoshie |
| 2010/0163057 A1 | 7/2010 | Anderson et al. |
| 2010/0174293 A1 | 7/2010 | Orban, III et al. |
| 2010/0217284 A1 | 8/2010 | Grace |
| 2010/0217528 A1 | 8/2010 | Sato et al. |
| 2010/0225209 A1 | 9/2010 | Goldberg et al. |
| 2010/0228264 A1 | 9/2010 | Robinson et al. |
| 2010/0228265 A1 | 9/2010 | Prisco |
| 2010/0234857 A1 | 9/2010 | Itkowitz et al. |
| 2010/0274087 A1 | 10/2010 | Diolaiti et al. |
| 2010/0291520 A1 | 11/2010 | Kurenov et al. |
| 2010/0317965 A1 | 12/2010 | Itkowitz et al. |
| 2010/0318099 A1 | 12/2010 | Itkowitz et al. |
| 2010/0318101 A1 | 12/2010 | Choi |
| 2010/0332031 A1 | 12/2010 | Itkowitz et al. |
| 2011/0015650 A1 | 1/2011 | Choi et al. |
| 2011/0050852 A1 | 3/2011 | Lamprecht et al. |
| 2011/0118707 A1 | 5/2011 | Burbank |
| 2011/0118748 A1 | 5/2011 | Itkowitz |
| 2011/0118753 A1 | 5/2011 | Itkowitz et al. |
| 2011/0137337 A1 | 6/2011 | van den Dool et al. |
| 2011/0190932 A1 | 8/2011 | Tsusaka et al. |
| 2011/0230894 A1 | 9/2011 | Simaan et al. |
| 2011/0238079 A1 | 9/2011 | Hannaford et al. |
| 2011/0276058 A1 | 11/2011 | Choi et al. |
| 2011/0279374 A1 | 11/2011 | Park et al. |
| 2011/0282493 A1 | 11/2011 | Ortmaier |
| 2011/0288579 A1 | 11/2011 | Hyodo |
| 2011/0306952 A1* | 12/2011 | Chen .................... A61B 17/29 606/1 |
| 2012/0071752 A1 | 3/2012 | Sewell et al. |
| 2012/0165828 A1 | 6/2012 | Duque et al. |
| 2012/0191245 A1 | 7/2012 | Fudaba et al. |

FOREIGN PATENT DOCUMENTS

| | | |
|---|---|---|
| CN | 101426412 A | 5/2009 |
| DE | 10 2008 041 867 A1 | 3/2010 |
| EP | 0 677 278 A1 | 10/1995 |
| EP | 1 728 475 A2 | 12/2006 |
| EP | 2 092 875 A1 | 8/2009 |
| EP | 2 298 220 A1 | 3/2011 |
| EP | 2 332 484 A2 | 6/2011 |
| JP | 63-029810 A | 2/1988 |
| JP | 64-034688 A | 2/1989 |
| JP | 01-271185 A | 10/1989 |
| JP | 02-071980 A | 3/1990 |
| JP | 02-292193 A | 12/1990 |
| JP | 03-161289 A | 7/1991 |
| JP | 05-096477 A | 4/1993 |
| JP | 5-329784 A | 12/1993 |
| JP | 07-001366 A | 1/1995 |
| JP | 07-194609 A | 8/1995 |
| JP | 07-241300 A | 9/1995 |
| JP | 07-246578 A | 9/1995 |
| JP | 07-96182 A | 10/1995 |
| JP | 8-66883 A | 3/1996 |
| JP | 08/215204 A | 8/1996 |
| JP | 08-243080 A | 9/1996 |
| JP | H10-502265 A | 3/1998 |
| JP | 10-128538 A | 5/1998 |
| JP | 11-300662 A | 11/1999 |
| JP | 2000-312684 A | 11/2000 |
| JP | 2001-087281 A | 4/2001 |
| JP | 2001-113481 A | 4/2001 |
| JP | 2001-277157 A | 10/2001 |
| JP | 2001-309920 A | 11/2001 |
| JP | 2002-014287 A | 1/2002 |
| JP | 2002-059380 A | 2/2002 |
| JP | 2002-102248 A | 4/2002 |
| JP | 2002-272758 A | 9/2002 |
| JP | 2002-537884 A | 11/2002 |
| JP | 2003-024336 A | 1/2003 |
| JP | 2003-053685 A | 2/2003 |
| JP | 2003-250812 A | 9/2003 |
| JP | 2003-265500 A | 9/2003 |
| JP | 2003-340752 A | 12/2003 |
| JP | 2004-105451 A | 4/2004 |
| JP | 2004-114201 A | 4/2004 |
| JP | 2005-511185 A | 4/2005 |
| JP | 2005-192743 A | 7/2005 |
| JP | 3686947 B2 | 8/2005 |
| JP | 2005-261827 A | 9/2005 |
| JP | 2005-283600 A | 10/2005 |
| JP | 2005-312991 A | 11/2005 |
| JP | 2006-061272 A | 3/2006 |
| JP | 2006-167867 A | 6/2006 |
| JP | 2006-288955 A | 10/2006 |

(56) References Cited

FOREIGN PATENT DOCUMENTS

| | | |
|---|---|---|
| JP | 2006-321027 A | 11/2006 |
| JP | 2007-029274 A | 2/2007 |
| JP | 2007-038315 A | 2/2007 |
| JP | 2007-98507 A | 4/2007 |
| JP | 2007-105485 A | 4/2007 |
| JP | 3999816 B2 | 10/2007 |
| JP | 2008-000282 A | 1/2008 |
| JP | 2008-036793 A | 2/2008 |
| JP | 4058113 B2 | 3/2008 |
| JP | 2008-093270 A | 4/2008 |
| JP | 2008-104854 A | 5/2008 |
| JP | 2008-514357 A | 5/2008 |
| JP | 2008-173724 A | 7/2008 |
| JP | 2008-188109 A | 8/2008 |
| JP | 4129313 B2 | 8/2008 |
| JP | 4176126 B2 | 11/2008 |
| JP | 2009-028157 A | 2/2009 |
| JP | 2009-056164 A | 3/2009 |
| JP | 2009-512514 A | 3/2009 |
| JP | 2009-520573 A | 5/2009 |
| JP | 2009-178230 A | 8/2009 |
| JP | 2009-178541 A | 8/2009 |
| JP | 2009-530037 A | 8/2009 |
| JP | 2009-195694 A | 9/2009 |
| JP | 2009-226029 A | 10/2009 |
| JP | 2009-226093 A | 10/2009 |
| JP | 2009-269127 A | 11/2009 |
| JP | 2010-504127 A | 2/2010 |
| JP | 2010-076012 A | 4/2010 |
| JP | 2010-524548 A | 7/2010 |
| JP | 2011-509112 A | 3/2011 |
| JP | 2011-206213 A | 10/2011 |
| JP | 2012-000199 A | 1/2012 |
| JP | 2012-012104 A | 1/2012 |
| JP | 2012-091310 A | 5/2012 |
| WO | 96/00044 A1 | 1/1996 |
| WO | 97/16123 A1 | 5/1997 |
| WO | 97/16124 A1 | 5/1997 |
| WO | 97/29690 A1 | 8/1997 |
| WO | 98/25666 A1 | 6/1998 |
| WO | WO 00/51486 A1 | 9/2000 |
| WO | 00/60421 A2 | 10/2000 |
| WO | WO 03/049596 A2 | 6/2003 |
| WO | 2006/039092 A2 | 4/2006 |
| WO | 2006/111966 A2 | 10/2006 |
| WO | WO 2007/047782 A2 | 4/2007 |
| WO | WO 2007/075864 A1 | 7/2007 |
| WO | 2007/111955 A2 | 10/2007 |
| WO | WO 2007/126443 A2 | 11/2007 |
| WO | WO 2007/138674 A1 | 12/2007 |
| WO | WO 2008/038184 A2 | 4/2008 |
| WO | WO 2008-108289 A1 | 9/2008 |
| WO | WO 2009/034477 A2 | 3/2009 |
| WO | 2009/089614 A1 | 7/2009 |
| WO | WO 2010/006057 A1 | 1/2010 |
| WO | 2010/093152 A2 | 8/2010 |
| WO | WO 2010/109932 A1 | 9/2010 |
| WO | 2010/126127 A1 | 11/2010 |
| WO | 2011/025786 A1 | 3/2011 |
| WO | 2011/060139 A2 | 5/2011 |
| WO | 2011/060185 A1 | 5/2011 |
| WO | 2011/060187 A1 | 5/2011 |
| WO | 2011/085815 A1 | 7/2011 |
| WO | WO 2012/042949 A1 | 4/2012 |

OTHER PUBLICATIONS

U.S. Office Action dated May 8, 2015 received in related U.S. Appl. No. 14/157,920.
Notice of Allowance dated Jan. 20, 2015 from related U.S. Appl. No. 13/566,023.
Notice of Allowance dated Jan. 29, 2015 from related U.S. Appl. No. 14/168,551.
Extended Supplementary European Search Report dated Feb. 12, 2015 from related European Application No. 12 81 9447.9.
Extended Supplementary European Search Report dated Feb. 13, 2015 from related European Application No. 12 82 0679.4.
Supplementary European Search Report dated Feb. 18, 2015 from related European Application No. 12 82 0758.6.
Extended Supplementary European Search Report dated Feb. 23, 2015 from related European Application No. 12 81 9877.7.
Extended Supplementary European Search Report dated Feb. 23, 2015 from related European Application No. 12 82 0239.7.
Partial Supplementary European Search Report dated Feb. 26, 2015 from related European Application No. 12 82 0066.4.
Partial Supplementary European Search Report dated Feb. 27, 2015 from related European Application No. 12 81 9672.2.
Extended Supplementary European Search Report dated Mar. 2, 2015 from related European Application No. 12 82 0017.7.
Extended Supplementary European Search Report dated Mar. 16, 2015 from related European Application No. 12 82 0479.9.
Extended Supplementary European Search Report dated Mar. 16, 2015 from related European Application No. 12 81 9504.7.
Extended Supplementary European Search Report dated Mar. 16, 2015 from related European Application No. 12 81 9398.4.
Office Action dated Mar. 25, 2015 received in related U.S. Appl. No. 14/169,321.
Extended Supplementary European Search Report dated Mar. 27, 2015 from related European Application No. 12 82 0056.5.
Chinese Office Action dated Jun. 3, 2015 from related Chinese Application No. 201280035926.3, together with an English language translation.
Chinese Office Action dated Jul. 1, 2015 from related Chinese Application No. 201280037244.6, together with an English language translation.
Extended Supplementary European Search Report dated Jul. 1, 2015 from related European Application No. 12 82 0066.4.
Extended Supplementary European Search Report dated Jul. 2, 2015 from related European Application No. 12 81 9672.2.
Extended Supplementary European Search Report dated Jul. 23, 2015 from related European Application No. 12 81 9455.2.
International Search Report dated Oct. 23, 2012 issued in PCT/JP2012/070414.
International Search Report dated Sep. 4, 2012 issued in PCT/JP2012/070408.
International Search Report dated Aug. 28, 2012 issued in PCT/JP2012/069927.
International Search Report dated Sep. 4, 2012 issued in PCT/JP2012/070415.
International Search Report dated Oct. 16, 2012 issued in PCT/JP2012/070581.
International Search Report dated Nov. 13, 2012 issued in PCT/JP2012/070576.
International Search Report dated Sep. 18, 2012 issued in PCT/JP2012/070417.
International Search Report dated Oct. 30, 2012 issued in PCT/JP2012/070418.
International Search Report dated Sep. 11, 2012 issued in PCT/JP2012/070416.
International Search Report dated Sep. 18, 2012 issued in PCT/JP2012/070407.
International Search Report dated Sep. 18, 2012 issued in PCT/JP2012/069868.
International Search Report dated Nov. 6, 2012 issued in PCT/JP2012/069919.
International Search Report dated Sep. 11, 2012 issued in PCT/JP2012/069696.
Office Action dated Sep. 16, 2015 received in related U.S. Appl. No. 13/566,012.
Office Action dated Oct. 19, 2015 received in related U.S. Appl. No. 14/168,525.
Office Action dated Oct. 22, 2015 received in related U.S. Appl. No. 14/151,987.
Office Action dated Nov. 19, 2015 received in related U.S. Appl. No. 14/157,920.

(56) References Cited

OTHER PUBLICATIONS

Office Action dated Mar. 10, 2016 received in related U.S. Appl. No. 13/566,012.
Japanese Office Action dated Jan. 19, 2016 from related Japanese Patent Application No. 2012-036226, together with an English language translation.
Office Action dated Mar. 24, 2016 received in related U.S. Appl. No. 13/566,047.
European Patent Office Communication dated May 23, 2016 in related European Application No. 12 819 877.7.
Office Action dated Jun. 16, 2016 received in related U.S. Appl. No. 14/169,742.
Japanese Office Action dated Jun. 28, 2016 in related Japanese Patent Application No. 2013-526973.
Japanese Office Action dated Apr. 26, 2016 from related Japanese Patent Application No. 2012-157788.
Japanese Office Action dated Apr. 26, 2016 from related Japanese Patent Application No. 2012-154945.
Notice of Allowance dated Apr. 22, 2016 issued in U.S. Appl. No. 14/157,920.
Office Action dated May 9, 2016 received in related U.S. Appl. No. 14/170,856.
Japanese Office Action dated Jun. 14, 2016 in related Japanese Patent Application No. 2012-012104.
Japanese Office Action dated Jan. 4, 2017 in related Japanese Patent Application No. 2012-012104.

\* cited by examiner

OPERATION SUPPORT DEVICE AND ATTACHMENT AND DETACHMENT METHOD THEREOF

This application is a continuation application based on PCT Patent Application No. PCT/JP2012/070415, filed Aug. 3, 2012, claiming priority based on Provisional Application No. 61/515,203 filed in U.S. on Aug. 4, 2011 and Japanese Patent Application No. 2012-023443 filed on Feb. 6, 2012, the contents of which are incorporated herein by reference.

BACKGROUND OF THE INVENTION

Field of the Invention

The present invention relates to an operation support device and an attachment and detachment method thereof.

Description of the Related Art

In the related art, an operation support device for performing operation support for a surgical operation is well known.

In such an operation support device, in order to sterilize a surgical instrument unit, it is necessary that the surgical instrument unit and a surgical instrument drive unit are attachably and detachably provided.

For example, as the operation support device, Japanese Patent No. 3686947 discloses an active forceps in which a forceps distal end body and a forceps shaft section, which constitute a surgical instrument unit, are detachably provided to a forceps base portion, which is a surgical instrument drive unit, at a proximal end portion of the forceps shaft section.

In the active forceps disclosed in Japanese Patent No. 3686947, in order to mount the surgical instrument unit, the forceps shaft section is inserted into a frame of the forceps base portion, the forceps shaft section is rotated 60 degrees about a center axis of the frame to fit a fitting member to a holder, and then a fastening screw of a clamp is fastened to fix the forceps shaft section to the frame.

SUMMARY OF THE INVENTION

According to a first aspect of the invention, an operation support device includes a connecting body in which a first support body configured to support a first shaft section so as to enable advance or retreat inside the first support body and a second support body configured to support a second shaft section so as to enable advance or retreat inside the second support body are detachably connected in a moving direction of the first shaft section and the second shaft section. The operation support device includes a first shaft engaging section formed at any one of the first shaft section and the second shaft section; a shaft connecting member installed at either the first shaft section or the second shaft section, at which the first shaft engaging section is not installed, and having a connection engaging section engaged with the first shaft engaging section; and a shaft fixing member movably installed with respect to the first shaft section or the second shaft section and, the shaft fixing member being configured to selectively form a first state in which the connection engaging section is held down to retain an engagement state such that the connection engaging section is engaged with the first shaft engaging section and a second state in which holding down the connection engaging section is released to release a shaft engagement in accordance with a moved position of the shaft fixing member.

According to a second aspect of the invention, in the operation support device according to the first aspect, the shaft fixing member may be configured to form the first state such that the first state is formed in the entire moving range in which the connection engaging section is moved in accordance with movement of the first shaft section and the second shaft section when the first shaft section and the second shaft section are connected to each other.

According to a third aspect of the invention, in the operation support device according to the first or second aspect, the operation support device may further include a support body engaging section installed at any one of the first support body and the second support body; a support body connecting member installed at any one of the first support body and the second support body at which the support body engaging section is not installed and having a support body connection engaging section engaged with the support body engaging section; and a support body fixing member movably installed with respect to the first support body or the second support body and configured to selectively form a third state in which the support body connection engaging section is held down to fix the engagement of the support body such that the support body connection engaging section is engaged with the support body engaging section and a fourth state in which held down the support body engaging section is released to release the engagement of the support body in accordance with a moved position of the support body fixing member.

According to a fourth aspect of the invention, in the operation support device according to the third aspect, the shaft fixing member and the support body fixing member may be integrated with each other and installed at the first support body or the second support body.

According to a fifth aspect of the invention, in the operation support device according to the third or fourth aspect, the shaft connecting member may be installed at the first shaft section, the first shaft engaging section may be installed at the second shaft section, and the shaft fixing member may be moved in a direction along the moving direction of the first shaft section and the second shaft section to form the first state or the second state and the third state or the fourth state, and the support body fixing member may be moved in a direction along the moving direction of the first shaft section and the second shaft section to form the third state or the fourth state.

According to a sixth aspect of the invention, in the operation support device according to any one of the first to fifth aspects, the operation support device may further include a surgical instrument unit; and a surgical instrument drive unit configured to transmit a driving force to the surgical instrument unit; wherein the connecting body may be formed by the surgical instrument unit and the surgical instrument drive unit, the first support body may be a surgical instrument drive unit support body installed at the surgical instrument drive unit, the first shaft section may be a surgical instrument drive unit shaft section configured to transmit the driving force of the surgical instrument drive unit, the second support body may be a surgical instrument unit support body installed at the surgical instrument unit, and the second shaft section may be a surgical instrument unit shaft section configured to transmit the driving force from the surgical instrument drive unit shaft section to the surgical instrument unit.

According to a seventh aspect of the invention, in the operation support device according to any one of the first to fifth aspects, the operation support device may further include a surgical instrument unit, a surgical instrument drive unit configured to transmit a driving force to the surgical instrument unit, and an intermediate member configured to connect the surgical instrument unit and the surgical instrument drive unit, wherein the connecting body may be formed by the intermediate member and the surgical instrument unit, the first support body may be an intermediate member support body installed at the intermediate member, the first shaft section may be an intermediate shaft section configured to transmit the driving force to the surgical instrument unit, the second support body may be a surgical instrument unit support body installed at the surgical instrument unit, and the second shaft section may be a surgical instrument unit shaft section configured to receive a driving force from the intermediate shaft section.

According to an eighth aspect of the invention, in the operation support device according to the sixth or seventh aspect of the invention, the shaft fixing member may have a shaft fixing member engaging section installed at the second support body and detachably engaged with the second shaft section, the second shaft section may have a second shaft engaging section detachably engaged with the shaft fixing member engaging section, and the shaft fixing member engaging section and the second shaft engaging section may be capable of engaging with each other in the second state and the engagement is released in the first state.

According to a ninth aspect of the invention, in the operation support device according to any one of the first to fifth aspects, the operation support device may further include a surgical instrument unit, a surgical instrument drive unit configured to transmit a driving force to the surgical instrument unit, and an intermediate member configured to connect the surgical instrument unit and the surgical instrument drive unit, wherein the connecting body may be formed between the surgical instrument drive unit and the intermediate member, the first support body may be a surgical instrument drive unit support body installed at the surgical instrument drive unit, the first shaft section may be a surgical instrument drive unit shaft section configured to transmit the driving force, the second support body may be an intermediate member support body installed at the intermediate member, and the second shaft section may be an intermediate shaft section configured to receive the driving force from the surgical instrument drive unit shaft section to transmit the driving force to the surgical instrument unit.

According to a tenth aspect of the invention, an attachment and detachment method of an operation support device includes a connecting body in which a first support body configured to support a first shaft section so as to enable advance or retreat inside the first support body and a second support body configured to support a second shaft section so as to enable advance or retreat inside the second support body are detachably connected in a moving direction of the first shaft section and the second shaft section; a first shaft engaging section installed at any one of the first shaft section and the second shaft section; and a shaft connecting member installed at either the first shaft section or the second shaft section at which the first shaft engaging section is not installed, and having a connection engaging section installed at the shaft section engaged with the first shaft engaging section. The attachment and detachment method includes, when the connecting body is formed, a shaft engagement process of engaging the first shaft engaging section with the connection engaging section by coming close the first support body and the second support body each other in the moving direction; and a shaft engagement fixing process of forming a first state in which an engagement state between the shaft connecting member and the first shaft engaging section is maintained, by moving a shaft fixing member movably installed with respect to the first shaft section or the second shaft section and holding down the connection engaging section, and when the connecting body is separated, a shaft engagement fixing release process of forming a second state in which engagement of the shaft is released by releasing holding down to the connection engaging section by moving the shaft fixing member from a position of the first state; and a shaft engagement release process of releasing the engagement between the first shaft section and the second shaft section by spacing the first support body and the second support body from each other in the moving direction.

According to an eleventh aspect of the invention, in the attachment and detachment method of the operation support device according to the tenth aspect, the operation support device may further include a support body engaging section installed at any one of the first support body and the second support body; a support body connecting member installed at any one of the first support body and the second support body at which the support body engaging section is not installed, and having a support body connection engaging section engaged with the support body engaging section; and a support body fixing member movably installed with respect to the first support body or the second support body and configured to selectively form a third state in which the support body connection engaging section is held down to fix the engagement of the support body such that the support body connection engaging section is engaged with the support body engaging section and a fourth state in which holding down to the support body engaging section is released to release the engagement of the support body in accordance with a moved position of the support body fixing member. The method may include, when the connecting body is formed, a support body engagement process of engaging the support body connection engaging section with the support body engaging section by approaching the first support body and the second support body each other in the moving direction; and a support body engagement fixing process of forming a third state in which an engagement state with the support body engaging section is maintained to fix the engagement of the support body, by moving a support body fixing member movably installed with respect to the first support body or the second support body to hold down the support body connection engaging section. The method includes, when the connecting body is separated, a support body engagement fixing release process of forming a fourth state in which holding down to the support body connection engaging section is released to release the engagement of the support body, by moving the support body fixing member from a position of the third state; and a support body engagement release process of releasing the engagement between the first support body and the second support body by spacing the first support body and the second support body from each other in the moving direction.

According to a twelfth aspect of the invention, in the attachment and detachment method of the operation support device according to the eleventh aspect, the shaft fixing member and the support body fixing member may be integrated and installed at the first support body or the second support body, the shaft engagement fixing process and the support body engagement fixing process may be performed in parallel, and the shaft engagement release process and the support body engagement release process may be performed in parallel.

DETAILED DESCRIPTION OF THE INVENTION

Figure 1:
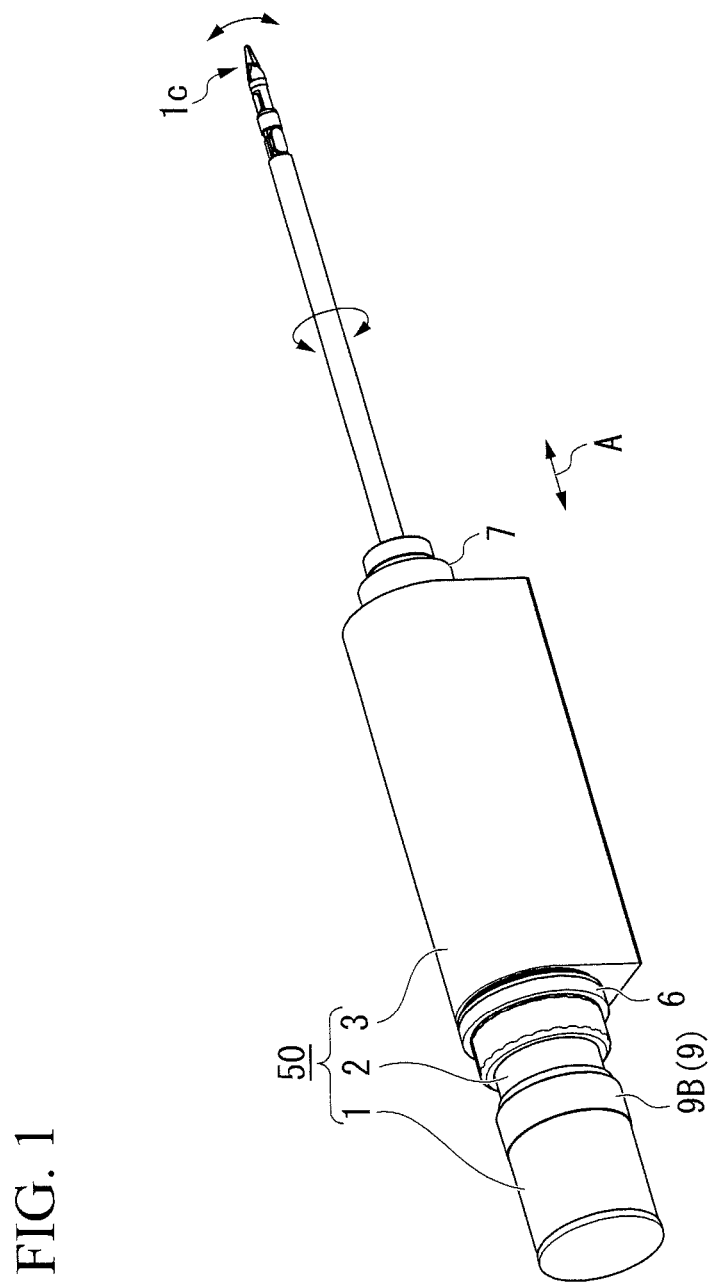
FIG. 1 is a schematic perspective view showing an appearance of an operation support device according to a first embodiment of the invention.

Hereinafter, embodiments of the invention will be described with reference to the accompanying drawings. Throughout the drawings, even when the embodiments are different, like or corresponding elements are designated by like reference numerals, and description thereof will not be repeated.

First Embodiment

An operation support device according to the first embodiment of the invention will be described.

FIG. 1 is a schematic perspective view showing an appearance of an operation support device according to the first embodiment.

Figure 2A:
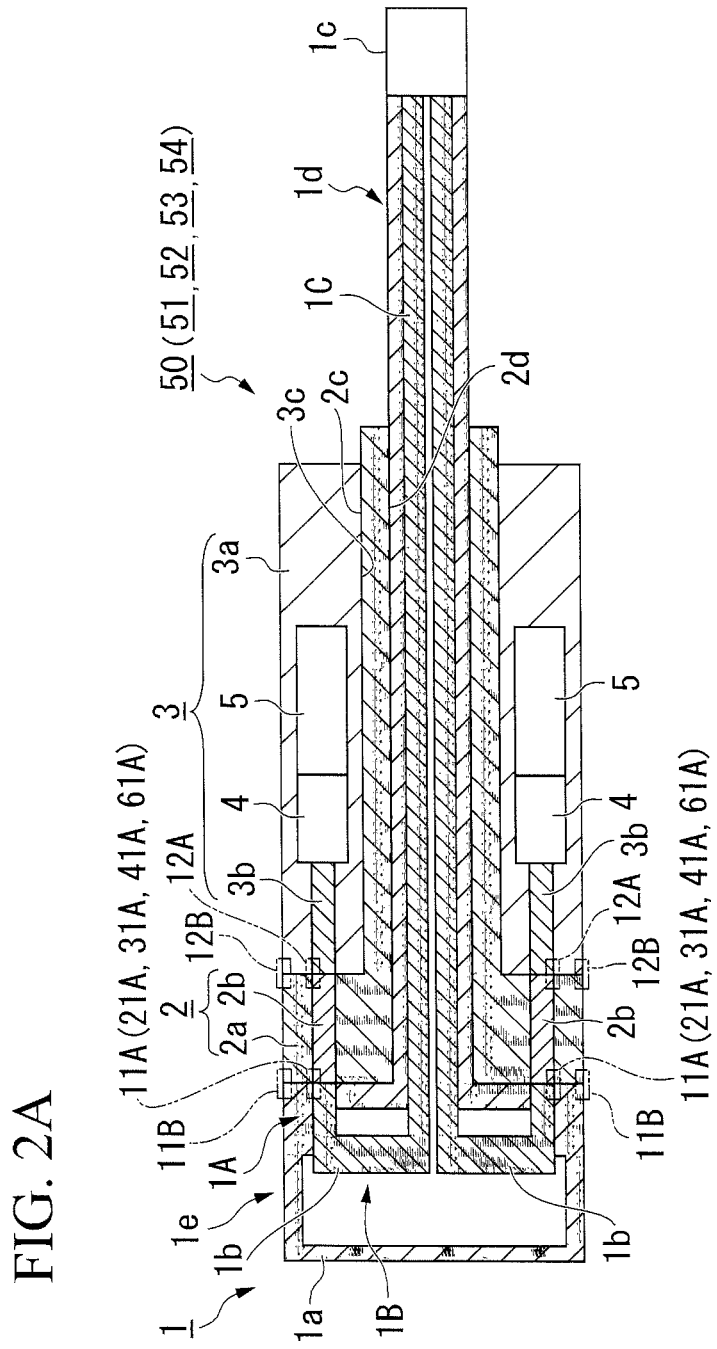
FIG. 2A is a schematic cross-sectional view in an axial direction showing major elements of the operation support device according to the first embodiment of the invention in connected state.
Figure 2B:
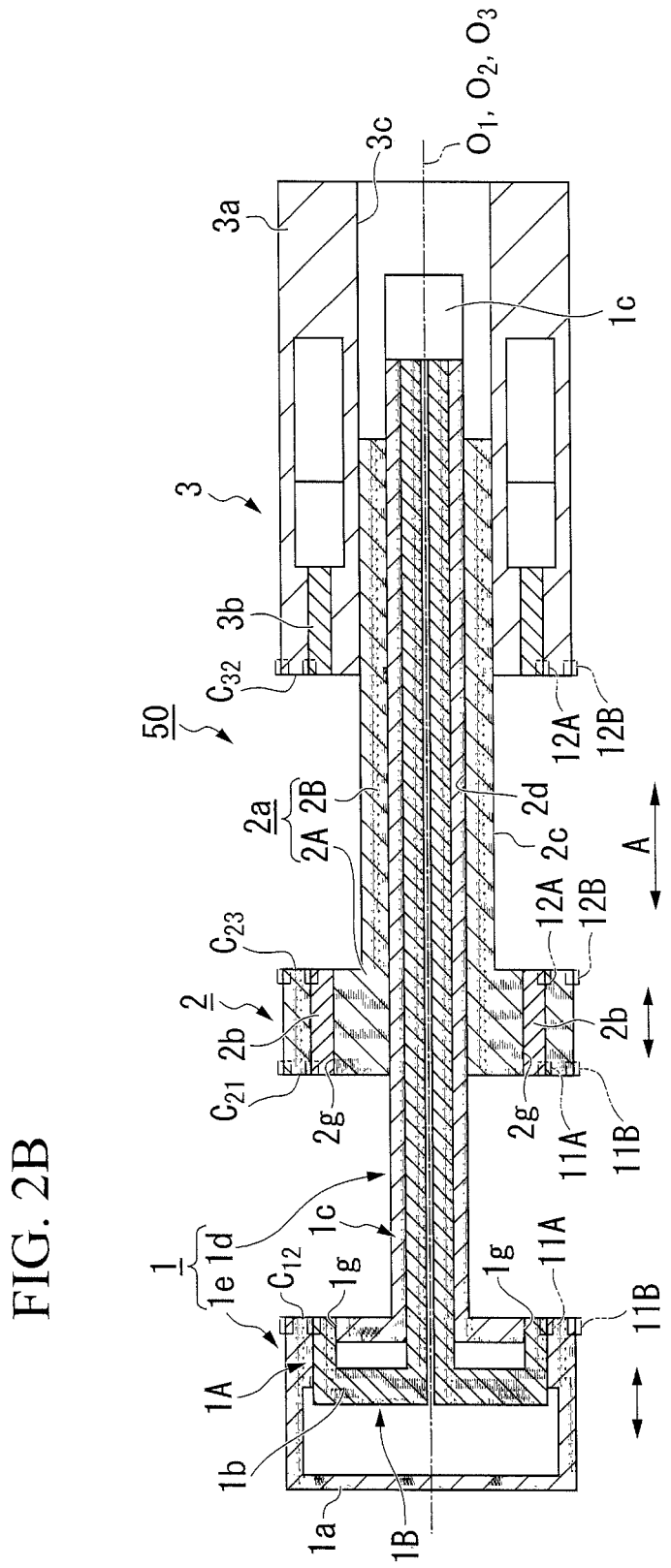
FIG. 2B is a schematic cross-sectional view in the axial direction showing the major elements of the operation support device according to the first embodiment of the invention in disconnected state.
Figure 3:
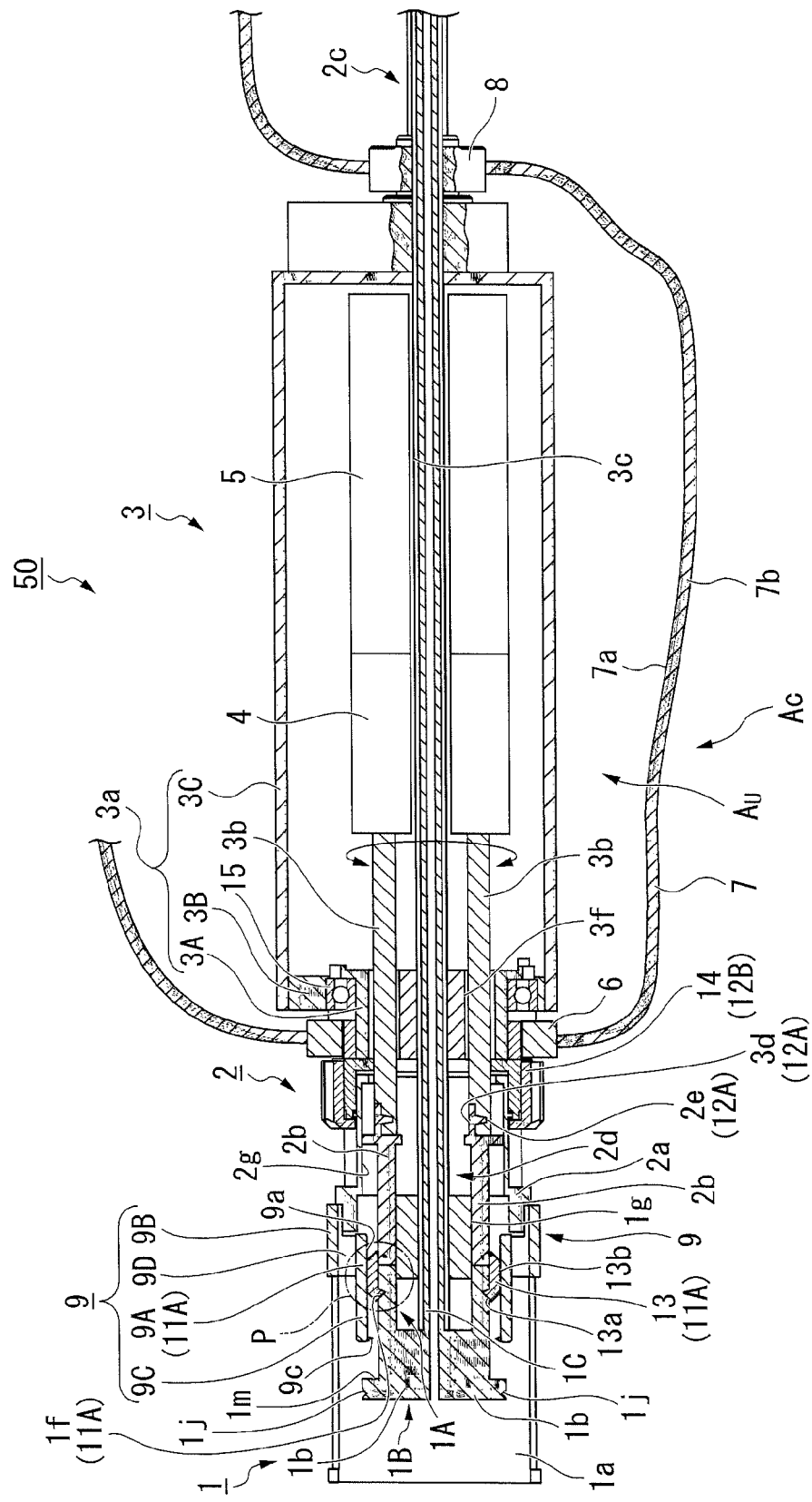
FIG. 3 is a schematic cross-sectional view in the axial direction showing a specific configuration of the operation support device according to the first embodiment of the invention.
Figure 4:
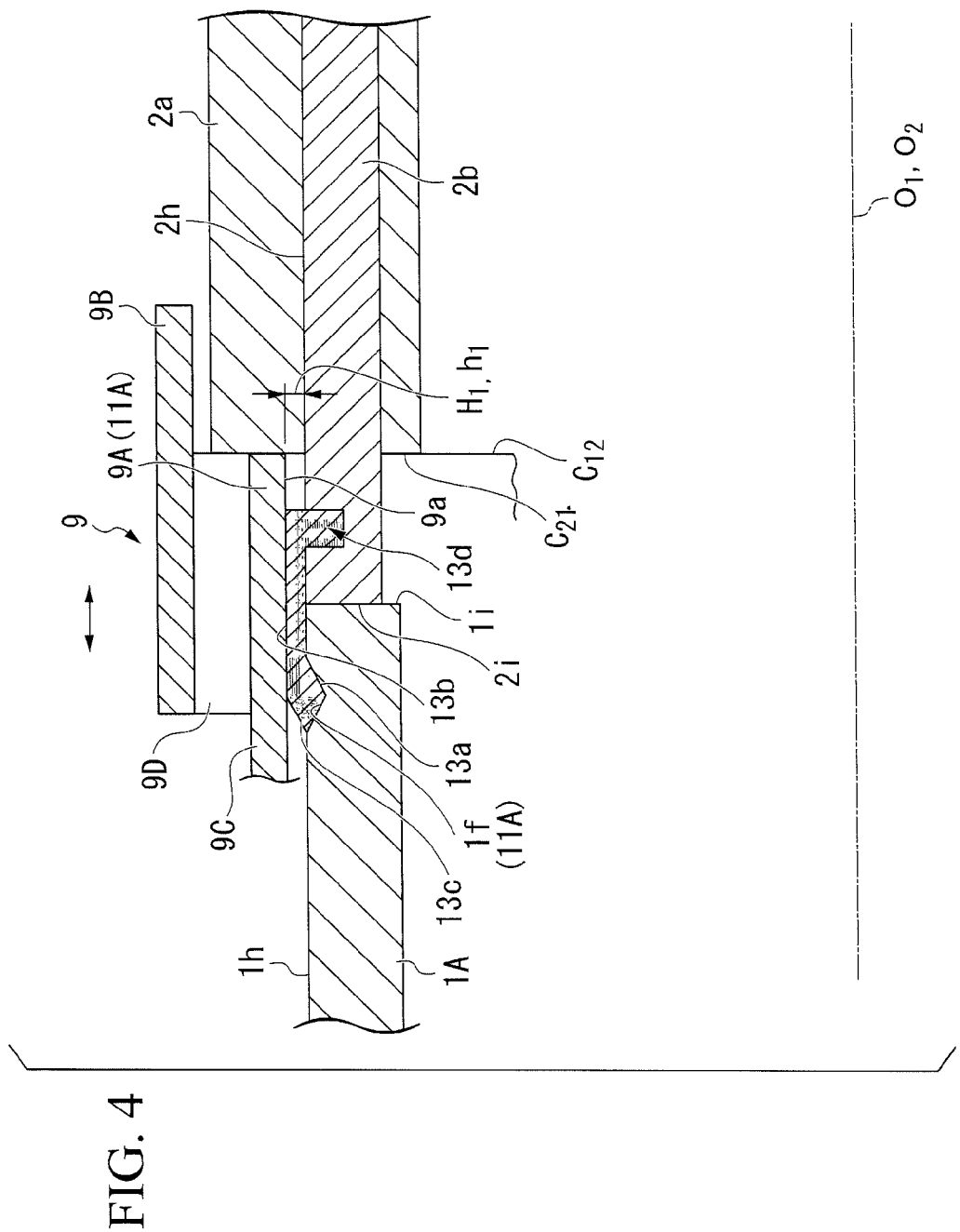
FIG. 4 is a partially enlarged view of a portion P in FIG. 3.
Figure 5:
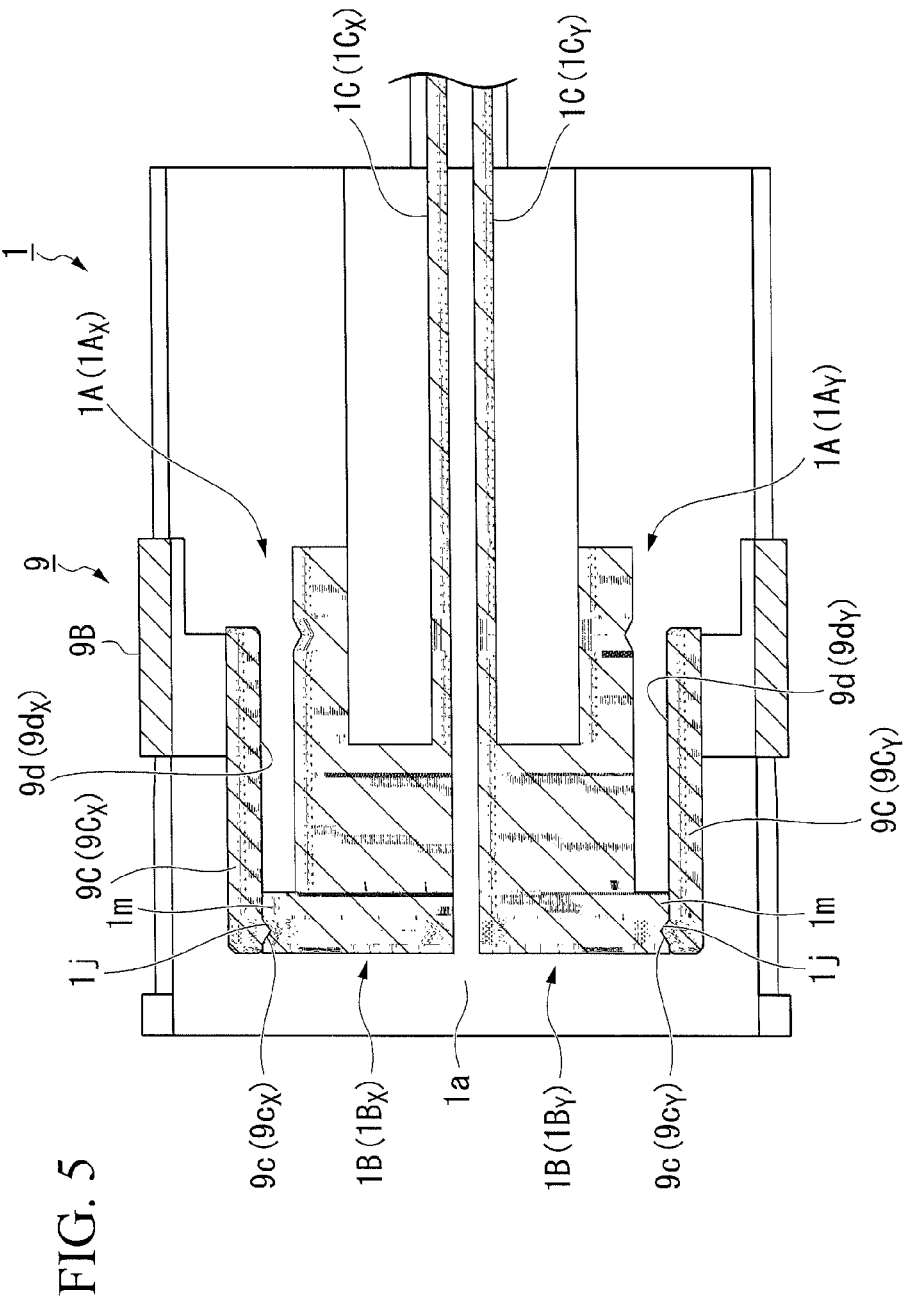
FIG. 5 is a schematic cross-sectional view in the axial direction showing a situation in which a shaft fixing member engaging section and a second shaft engaging section of the operation support device according to the first embodiment of the invention are engaged with each other.
Figure 6A:
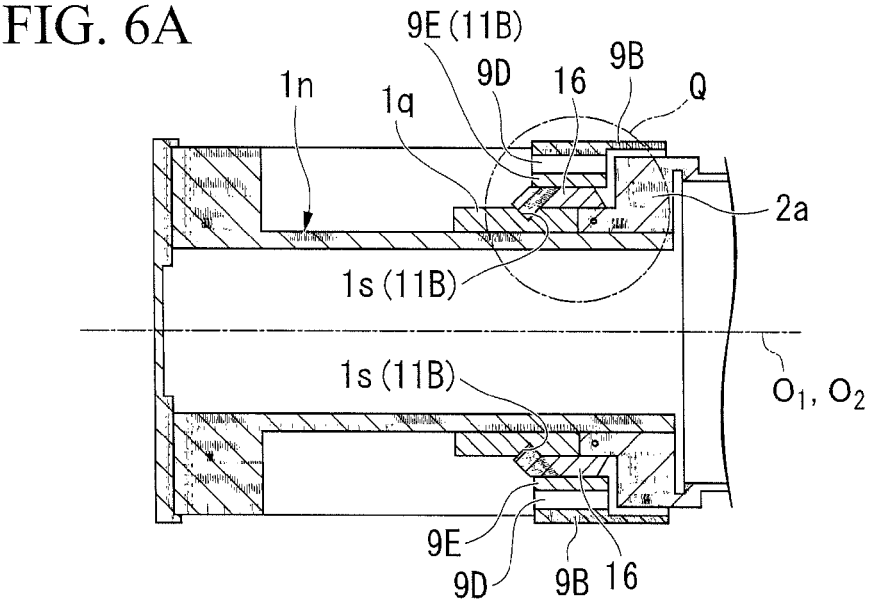
FIG. 6A is a schematic cross-sectional view in the axial direction showing a configuration of major parts of a surgical instrument unit and an intermediate member of the operation support device according to the first embodiment of the invention.
Figure 6B:
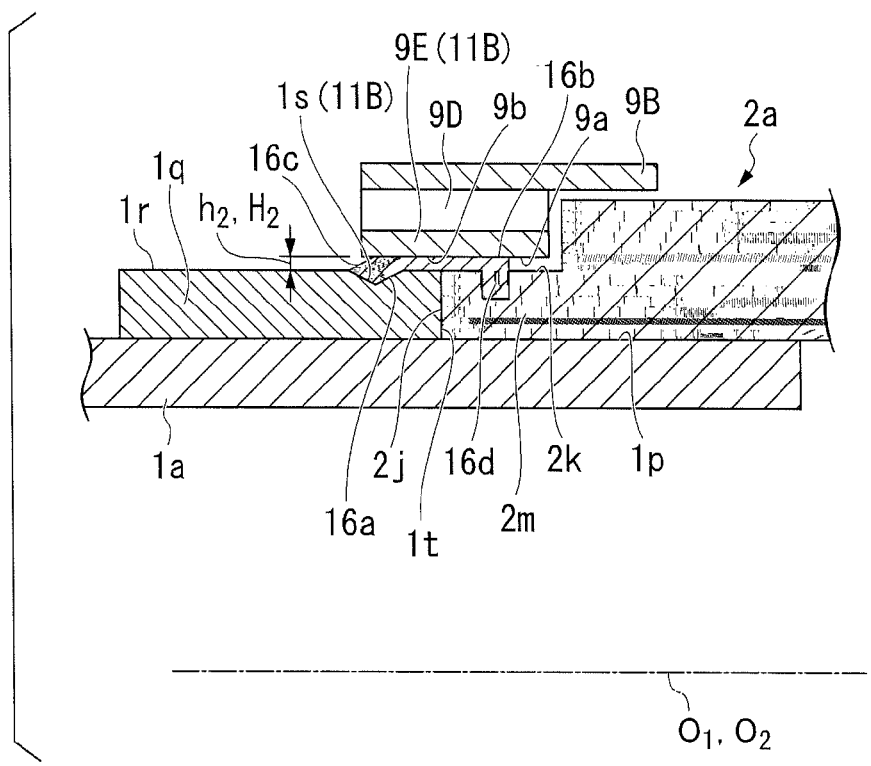
FIG. 6B is a partially enlarged view of a portion Q in FIG. 6A.

FIG. 2A is a schematic cross-sectional view in an axial direction showing major elements of the operation support device according to the first embodiment in connected state. FIG. 2B is a schematic cross-sectional view in the axial direction showing the major elements of the operation support device according to the first embodiment in disconnected state. FIG. 3 is a schematic cross-sectional view in the axial direction showing a specific configuration of the operation support device according to the first embodiment. FIG. 4 is a partially enlarged view of a portion P in FIG. 3. FIG. 5 is a schematic cross-sectional view in the axial direction showing a situation in which a shaft fixing member engaging section and a second shaft engaging section are engaged with each other in the operation support device according to the first embodiment. FIG. 6A is a schematic cross-sectional view in the axial direction showing a configuration of major parts of a surgical instrument unit and an intermediate member of the operation support device according to the first embodiment. FIG. 6B is a partially enlarged view of a portion Q of FIG. 6A.

As shown in FIG. 1, an operation support device 50 according to the embodiment is, for example, an apparatus for operating a surgical instrument and moving the surgical instrument in a state in which the surgical instrument is disposed at an appropriate position of a body cavity or the like of a patient during a surgical operation.

The operation support device 50 includes a surgical instrument drive unit 3, an intermediate member 2, and a surgical instrument unit 1. The surgical instrument drive unit 3 and the intermediate member 2 are detachably connected to each other in an axial direction shown by an arrow A in FIG. 1. In addition, the intermediate member 2 and the surgical instrument unit 1 are detachably connected to each other in the axial direction shown by the arrow A in FIG. 1. Accordingly, the operation support device 50 has a substantially shaft-shaped profile extending from a proximal end side to a distal end side.

Here, the distal end side of the operation support device 50 in use is a side of a body cavity of a patient, and the proximal end side is an opposite side thereof.

Hereinafter, even in the description of the parts of the operation support device 50, when a relative positional relationship of the operation support device 50 in a connection state in a longitudinal direction is shown, the distal end side, the proximal end side, the distal end portion, the proximal end portion, and so on, are referred to as described above unless specifically indicated otherwise.

In addition, when a direction related to a member having a cylindrical shape, a column shape, a shaft shape or the like in which a center axis is capable of being specified is described, a direction along the center axis may be referred to as an axial direction; a direction about the center axis may be referred to as a circumferential direction; and a direction perpendicular to the center axis may be referred to as a radial direction.

In FIG. 1, while a forceps is shown as one kind of the surgical instrument to be installed at the surgical instrument unit 1, this is an example. As long as a surgical instrument can transmit a driving force by a linear movement element such as an operating rod, an operating wire, or the like is used as the surgical instrument installed at the surgical instrument unit 1, the kind of surgical instrument is not particularly limited. In addition to the forceps, the surgical instrument may be, for example, a stapler, an endoscope having a distal end portion for which a curve motion is possible, or the like.

The operation support device 50 is capable of being mounted on, for example, an end portion of an arm (not shown) having joints with multiple degrees of freedom. Such an arm may be a slave arm of a medical manipulator system, which is a master slave type. In this case, the surgical instrument drive unit 3 of the operation support device 50 may be electrically connected to a control unit of the medical manipulator system and perform a motion based on a control signal from a master arm to configure a part of the slave arm.

However, the operation support device 50 is not limited to uses such as a support with such an arm, a use as a portion of the medical manipulator system, or the like, for example, but an operator can manually hold and use the operation support device 50.

The surgical instrument drive unit 3 is a member configured to generate a displacement or a force (hereinafter, simply referred to as "a driving force") to run the surgical instrument unit 1 based on a control signal from a drive control unit (not shown) and transmit the displacement or force to the surgical instrument unit 1. A transmission path of the driving force may be indirect or direct. In the embodiment, as described below, the driving force may be indirectly transmitted via an intermediate shaft 2b of the intermediate member 2.

The surgical instrument drive unit 3 includes a surgical instrument drive unit support body 3a as shown in FIGS. 2A and 2B.

The surgical instrument drive unit support body 3a is a member formed a column-shaped profile and having an intermediate member insertion hole 3c. The intermediate member insertion hole 3c is formed at a position coaxial with a center axis $O_3$ of the profile and has a size appropriate for allowing insertion of the intermediate member 2.

A connecting end portion $C_{32}$ in contact with the intermediate member 2 in connected state is formed at one end side (a left side of FIG. 2B) in the axial direction of the surgical instrument drive unit support body 3a.

A motor unit 5, a linear movement conversion unit 4, and a drive force transmission shaft 3b are mounted inside the surgical instrument drive unit support body 3a.

FIG. 2A and FIG. 2B schematically show a simplified connection relationship, and specific features are appropriately omitted or exaggerated. For example, although an end portion of the drive force transmission shaft 3b is shown at a position aligned with the connecting end portion $C_{32}$, in an actual connecting motion, as described below, the end portion protrudes toward the intermediate member 2.

The motor unit 5 is a motor rotated based on a control signal from a drive control unit, and an output shaft is connected to the linear movement conversion unit 4. The drive control unit and the output shaft of the motor are not shown. As a specific configuration of the motor unit 5, for example, a DC motor, or the like may be employed.

The linear movement conversion unit 4 is a member configured to convert a rotation output of the motor unit 5 into a linear movement in a direction along the center axis $O_3$ of the intermediate member insertion hole 3c. A configuration of the linear movement conversion unit 4 is not particularly limited as long as rotation is capable of being converted into linear movement, and for example, a lead screw mechanism, or the like may be employed.

The drive force transmission shaft 3b is a shaft member linearly driven by the linear movement conversion unit 4. The drive force transmission shaft 3b is movably supported in a direction parallel to the center axis $O_3$ at a position spaced apart from the center axis $O_3$ in a radial direction in the surgical instrument drive unit support body 3a.

In addition, the drive force transmission shaft 3b is disposed in the vicinity of the connecting end portion $C_{32}$. The drive force transmission shaft 3b can protrude toward the intermediate member 2 rather than the connecting end portion $C_{32}$ or can retreat toward the surgical instrument drive unit 3 according to necessity. In the embodiment, as shown in FIG. 3, an end portion of the drive force transmission shaft 3b is connected to the intermediate member 2 side in a protruding state.

A cross-sectional shape of the drive force transmission shaft 3b perpendicular to the axial direction is not particularly limited, but, for example, a rectangular cross-section may be employed.

The drive force transmission shaft 3b, the linear movement conversion unit 4, and the motor unit 5 may be set to an appropriate number of one or more according to the number of driving inputs necessary to drive the surgical instrument unit 1.

Hereinafter, as shown in FIG. 2B, as an example, the case in which a pair of members have the same positional relationship such that the members are line-symmetrical with respect to the center axis $O_3$ will be described.

For this reason, in the drawings, when it is apparent that the members having the same shape are disposed line-symmetrically with respect to a center axis such as the center axis $O_3$, for the convenience of illustration, a reference numeral of one side may be omitted or a reference numeral corresponding to one member may designate both symmetrical members.

Next, a specific configuration of the surgical instrument drive unit support body 3a according to the embodiment will be described with reference to FIG. 3.

In the embodiment, the surgical instrument drive unit support body 3a includes a support main body 3A, a side plate portion 3B, and a housing 3C. The support main body 3A is positioned in a radial direction and the circumferential direction of each of the drive force transmission shafts 3b in an end portion of the proximal end side and is slidably held in the axial direction. The support main body 3A has the intermediate member insertion hole 3c formed therein. The side plate portion 3B is held the support main body 3A to enable rotation via a bearing 15 at the proximal end side of the support main body 3A. The housing 3C is fitted onto an outer circumference side of the side plate portion 3B to cover an outer circumference side of the surgical instrument drive unit support body 3a.

Each of the linear movement conversion unit 4 and the motor unit 5 is fixed inside the support main body 3A.

A rotary motor (not shown) is installed at an inner circumferential portion of the housing 3C. For example, the support main body 3A is capable of being rotated about the center axis $O_3$ (see FIG. 2B) via a belt driving mechanism, or the like.

In the embodiment, the connecting end portion $C_{32}$ of the surgical instrument drive unit support body 3a is formed at an end portion of the proximal end side of the support main body 3A.

The intermediate member 2 is a member configured to make the surgical instrument drive unit 3 and the surgical instrument unit 1 to detachably connect. The intermediate member 2 is a member configured to transmit a driving force from the surgical instrument drive unit 3 toward the surgical instrument unit 1. In addition, the intermediate member 2 is installed to connect the sterilized surgical instrument unit 1 to the surgical instrument drive unit 3 with no direct contact.

As shown in FIG. 2B, the intermediate member 2 is a substantially cylindrical member around the center axis $O_2$, and includes an intermediate member support body 2a (a first support body), and the intermediate shaft 2b (an intermediate shaft section, a first shaft section). The intermediate member support body 2a has a connecting section 2A and a cylindrical section 2B disposed from the proximal end side toward the distal end side. The intermediate shaft 2b is a member that is detachably engaged with each of the drive force transmission shafts 3b of the surgical instrument drive unit 3 and receives a driving force from each of the drive force transmission shafts 3b to transmit the driving force toward the surgical instrument unit 1 in engagement state. The number of drive force transmission shafts 3b is equal to the number of intermediate shafts 2b.

The connecting section 2A is a part of a support body spread in an annular region sandwiched between the connecting end portion $C_{23}$ and the connecting end portion $C_{21}$. The connecting end portion $C_{23}$ is in contact with the connecting end portion $C_{32}$ of the surgical instrument drive unit 3 in the axial direction in a connected state. The connecting end portion $C_{21}$ is formed at the proximal end portion opposite to the connecting end portion $C_{23}$ to be in contact with the surgical instrument unit 1 in the axial direction in a connected state.

A guide groove 2g is formed to pass through the connecting section 2A from the connecting end portion $C_{23}$ toward the connecting end portion $C_{21}$. The guide groove 2g positions each of the intermediate shafts 2b at a position in the circumferential direction and the radial direction to be held, and is slidably held in the axial direction.

Each of the intermediate shafts 2b is positioned to oppose each of driving force transmission members 1b of the surgical instrument unit 1 in connected state and oppose each of the drive force transmission shafts 3b of the surgical instrument drive unit 3 by the guide groove 2g.

In addition, while not shown, an appropriate positioning unit is installed at the connecting section 2A to position in the circumferential direction of the intermediate member 2 with respect to the surgical instrument drive unit 3 and the surgical instrument unit 1.

The cylindrical section 2B is a cylindrical support section inserted to pass through the intermediate member insertion hole 3c of the surgical instrument drive unit support body 3a. The cylindrical section 2B includes an outer circumferential insertion portion 2c fitted into the intermediate member insertion hole 3c.

A surgical instrument unit insertion hole 2d into which the surgical instrument unit 1 is capable of being inserted is formed to pass through center portions of the connecting section 2A and the cylindrical section 2B in the axial direction.

A shape of a cross-section perpendicular to the axial direction of the intermediate shaft 2b is not particularly limited. In the embodiment, as an example, a rectangular cross-section having two sides opposite to each other in the radial direction of the intermediate member 2 is employed.

As shown in FIG. 2A, a support body attachment and detachment mechanism unit 12B and a shaft attachment and detachment mechanism unit 12A are installed between the intermediate member 2 and the surgical instrument drive unit 3. The support body attachment and detachment mechanism unit 12B detachably engages the intermediate member support body 2a with the surgical instrument drive unit support body 3a. The shaft attachment and detachment mechanism unit 12A detachably engages the intermediate shaft 2b with the drive force transmission shaft 3b.

In the embodiment, as shown in FIG. 3, the support body attachment and detachment mechanism unit 12B is fixed by a well-known fixing ring 14 for locking after engagement with an engaging section (not shown) in a state in which the intermediate member support body 2a is in contact with the proximal end portion of the support main body 3A is employed.

However, when the engagement is fixed by the fixing ring 14, a drape ring 6 is fitted onto an outer circumferential portion of an end portion of the distal end side of the intermediate member support body 2a. The drape ring 6 is fixed while interposed between the support body attachment and detachment mechanism unit 12B and the surgical instrument drive unit 3.

The drape ring 6 is a ring member in close contact with a drape 7 configured to cover the surgical instrument drive unit 3. By the drape ring 6, a through-hole having a size equal to an inner diameter of the drape ring 6 is formed at a portion of the drape 7.

In the embodiment, a drape ring 8 is installed at another position of the drape 7. The drape ring 8 is fitted onto the distal end portion of the intermediate member 2 passing through from the surgical instrument drive unit 3 to the distal end side. According to the configuration, the drape rings 6 and 8 are fixed to the proximal end side and the distal end side of the intermediate member 2 in an opposite positional relationship, and the surgical instrument drive unit 3 is sandwiched between the drape rings 6 and 8.

For this reason, as shown in FIG. 3, in the operation support device 50, the surgical instrument drive unit 3 is disposed at a first region $A_U$ covered by one surface 7a of the drape 7. The surgical instrument unit 1 faces a surface 7b opposite to the surface 7a, and is disposed at a second region $A_C$ separated from the first region $A_U$, which is bounded by the drape 7 and the intermediate member 2.

In addition, in the embodiment, the drape 7 is attached via the drape rings 6 and 8. The drape 7 is formed of a sheet-shaped member having flexibility such as sterilized polyethylene. Further, for example, a hole may be formed in the drape 7 to directly pass through the cylindrical section 2B, not via the drape rings 6 and 8, and a reinforcement member may be provided to prevent breakage of the hole.

In the embodiment, as shown in FIG. 3, the shaft attachment and detachment mechanism unit 12A is constituted by a shaft engaging section 3d and a shaft engaging section 2e.

The shaft engaging section 3d is formed at an end portion of the drive force transmission shaft 3b, which becomes the proximal end side of the surgical instrument drive unit 3.

The shaft engaging section 2e is configured to detachably engage with the shaft engaging section 3d formed at the end portion of the intermediate shaft 2b which becomes a distal end side of the intermediate member 2.

A specific well-known configuration in which the shaft engaging sections 3d and 2e are constituted by concave and convex portions that are detachably engaged with each other may be employed.

As shown in FIG. 1, FIG. 2A and FIG. 2B, the surgical instrument unit 1 includes an operation unit 1c disposed at the distal end side and configured to operate a subject to be operated. The surgical instrument unit 1 is constituted that the operation unit 1c is driven by the driving force transmitted from the surgical instrument drive unit 3 via the intermediate member 2 to operate the subject to be operated. The surgical instrument unit 1 is detachably installed with respect to the intermediate member 2 in the axial direction.

When the operation unit 1c of the surgical instrument unit 1 is configured to be run by one or more driving forces in one axial direction, an appropriate configuration is capable of being employed. For example, a configuration such as a forceps constituted by two forceps pieces, a joint for varying a direction of the forceps, an outer cylindrical tube having one or more joints, a curved portion of an endoscope that is capable of being curved in one or two directions, or the like may be employed.

As shown in FIG. 2B, a schematic configuration of the surgical instrument unit 1 is a substantially shaft-shaped member, and includes a surgical instrument unit support body 1a (a second support body) and the driving force transmission members 1b. The surgical instrument unit support body 1a is connected to the intermediate member 2. The driving force transmission members 1b are detachably engaged with the intermediate shafts 2b of the intermediate member 2. The intermediate shafts 2b are members configured to receive driving forces from intermediate shafts 2b to transmit the driving forces toward the operation unit 1c in connected state. The number of intermediate shafts 2b is equal to the number of drive force transmission members 1b.

The surgical instrument unit support body 1a has the connecting end portion $C_{12}$ in contact with the connecting end portion $C_{21}$ of the intermediate member 2 in connected state. A box-shaped portion 1e and a cylindrical portion 1d are formed at the surgical instrument unit support body 1a. The box-shaped portion 1e movably supports part of the driving force transmission member 1b therein in the same direction as the moving direction of the intermediate shaft 2b in connected state. The cylindrical portion 1d is coaxial with a center axis $O_1$ of the box-shaped portion 1e and extends toward the distal end side.

A guide groove 1g, in which an end portion of each of the driving force transmission members 1b is slidably held in the axial direction, is formed in the inside of the box-shaped portion 1e adjacent to the connecting end portion $C_{12}$.

By the guide groove 1g, each of the driving force transmission members 1b is positioned in the circumferential direction and the radial direction that can oppose each of the intermediate shafts 2b of the intermediate member 2 upon connection.

The cylindrical portion 1d has an outer diameter that is capable of being inserted into the surgical instrument unit insertion hole 2d of the intermediate member 2, and is configured to be larger than a length of the surgical instrument unit insertion hole 2d. The operation unit 1c is connected to the distal end portion of the cylindrical portion 1d.

The driving force transmission member 1b is a shaft-shaped member having a shape curved into substantially a J shape, and includes an input-side transmission shaft section 1A (a surgical instrument unit shaft section, a second shaft section), a connecting section 1B, and an output-side transmission shaft section 1C.

The input-side transmission shaft section 1A is a shaft section configured to be capable of being engaged with the intermediate shaft 2b and receive a driving force from the intermediate shaft 2b upon engagement with the intermediate shaft 2b. The input-side transmission shaft section 1A is movably held in the axial direction parallel to the center axis $O_1$ by the guide groove 1g of the box-shaped portion 1e.

A shape of a cross-section perpendicular to the axial direction of the input-side transmission shaft section 1A is not particularly limited, but in the embodiment, as an example, a rectangular cross-section having two sides opposite to each other in the radial direction of the surgical instrument unit 1 is employed.

The connecting section 1B is a section formed from the end portion of the proximal end side of the input-side transmission shaft section 1A toward the center axis $O_1$ and connecting the end portion of the proximal end side of the output-side transmission shaft section 1C to the end portion of the proximal end side of the input-side transmission shaft section 1A.

In the embodiment, as shown in FIG. 3 (not shown in FIG. 2A and FIG. 2B), a step-shaped protrusion section 1m protruding outward in the radial direction is formed at the proximal end side of the connecting section 1B. A concave engaging section 1j (a second shaft engaging section) for engagement with an engaging protrusion 9c of a rod-shaped portion 9C, which will be described below, is formed at the end portion in the radial direction of the step-shaped protrusion section 1m.

The output-side transmission shaft section 1C is a shaft section extending from the connecting section 1B parallel to the center axis $O_1$ toward the distal end side of the surgical instrument unit 1. The output-side transmission shaft section 1C is accommodated in the box-shaped portion 1e and the cylindrical portion 1d, and the distal end portion thereof is connected to the operation unit 1c.

The output-side transmission shaft section 1C is capable of being connected to an appropriate member that can operate the operation unit 1c, for example, a link, a rod/wire, or the like. When the operation unit 1c is a curved portion of an endoscope, or the like, a shaft section having a flexibility that is capable of being curved may be employed as the output-side transmission shaft section 1C.

While the driving force transmission member 1b may be configured by appropriately attaching a plurality of members formed of separate materials appropriate for the input-side transmission shaft section 1A, the connecting section 1B, and the output-side transmission shaft section 1C, the members may be integrally formed with each other.

As shown in FIG. 2A, a shaft attachment and detachment mechanism unit 11A and a support body attachment and detachment mechanism unit 11B are installed between the surgical instrument unit 1 and the intermediate member 2. The shaft attachment and detachment mechanism unit 11A is detachably engaged with the input-side transmission shaft section 1A and the intermediate shaft 2b. The support body attachment and detachment mechanism unit 11B is detachably engaged with the surgical instrument unit support body 1a and the intermediate member support body 2a.

Here, the shaft attachment and detachment mechanism unit 11A has the same number and the same configuration of members as the input-side transmission shaft section 1A and the intermediate shaft 2b.

The support body attachment and detachment mechanism unit 11B may be installed in at least one place, or may be installed at a plurality of places spaced apart from each other in the circumferential direction. Hereinafter, as an example, a case in which a pair of units are installed to oppose each other with the center axes $O_1$ and $O_2$ interposed therebetween will be described.

In addition, since FIG. 2A and FIG. 2B are schematic views, in order to avoid overlapping with the shaft attachment and detachment mechanism unit 11A, the support body attachment and detachment mechanism unit 11B is shown at the outer circumferential portions of the surgical instrument unit support body 1a and the intermediate member support body 2a. However, the support body attachment and detachment mechanism unit 11B may be installed at the outer circumferential portions of the surgical instrument unit support body 1a and the intermediate member support body 2a or may be installed therein. In the following specific configuration, a case in which the unit is installed therein will be described as an example.

In the embodiment, as shown in FIG. 3, the shaft attachment and detachment mechanism unit 11A includes a concave engaging section 1f (a first shaft engaging section), a hook portion 13 (a shaft connecting member), and an attachment and detachment ring 9 (a shaft fixing member, support body fixing member).

The concave engaging section 1f is a shaft engaging section configured to engage the input-side transmission shaft section 1A with the intermediate shaft 2b. As shown in FIG. 4, the concave engaging section 1f is formed at an outer circumference side surface 1h outside in the radial direction (an upper side of FIG. 4) in the distal end side (a right side of FIG. 4) of the input-side transmission shaft section 1A. In the embodiment, the concave engaging section 1f has a groove portion with a V-shaped cross-section in the axial direction.

In the embodiment, a position in the axial direction, the concave engaging section 1f is formed so that a positional relationship in which a distal end surface 1i of the input-side transmission shaft section 1A is in contact with a proximal end surface 2i of the intermediate shaft 2b when the hook portion 13 (to be described below) is engaged therewith. However, according to conditions of a shape or strength of the hook portion 13, when there is no obstruction in transmission of the driving force, the concave engaging section 1f may be formed so that a positional relationship in which the engagement is maintained with the distal end surface 1i and the proximal end surface 2i spaced apart from each other.

The hook portion 13 is a rod-shaped member having substantially the same width (a width in the depth direction of FIG. 4) as of the intermediate shaft 2b and the input-side transmission shaft section 1A. The hook portion 13 is pivotally fixed to the proximal end portion of the intermediate shaft 2b at one end side thereof via a hinge portion 13d, and disposed on an outer circumference side surface 2h outside in the radial direction of the intermediate shaft 2b. However, a pivot range of the hook portion 13 may be a small angular range such that an engaging protrusion 13a which will be described below, moves to substantially the same position as the outer circumference side surface 2h.

In addition, the hinge portion 13d may include, for example, an elastic member or a spring to hold down the hook portion 13 in a direction to be in close contact with the outer circumference side surface 2h.

Further, the hook portion 13 has a length in which the other end portion thereof protrudes toward the proximal end side rather than the proximal end surface 2i of the intermediate shaft 2b in a posture in which the hook portion 13 is parallel to the intermediate shaft 2b as shown in FIG. 4. The engaging protrusion 13a (a shaft connection engaging section) having an angle cross-section engaged with the concave engaging section 1f is formed at the other end portion inside in the radial direction.

The engaging protrusion 13a is installed at a position such that the engaging protrusion 13a is capable of being completely engaged with the concave engaging section 1f in a state in which the distal end surface 1i of the input-side transmission shaft section 1A abuts the proximal end surface 2i of the intermediate shaft 2b, and the outer circumference side surfaces 1h and 2h are aligned with each other.

In the hook portion 13, a thickness of the intermediate section, excluding the engaging protrusion 13a and the hinge portion 13d, is set as $h_1$. For this reason, in the engagement state shown in FIG. 4, an outer circumferential surface 13b of the hook portion 13 has a flat surface protruding from the outer circumference side surfaces 1h and 2h outward in the radial direction by a height $h_1$.

In the other end side of the engaging protrusion 13a, a taper 13c inclined from one end side of the outer circumferential surface 13b toward the other end is formed at a rear side of the engaging protrusion 13a. Even in a state in which the distal end surface 1i comes into contact with the proximal end surface 2i, due to disturbance such as gravity, or the like, the engaging protrusion 13a may not be engaged with the concave engaging section 1f. In this case, an inner circumference pressing section 9A is allowed to be in contact with the taper 13c to hold down the engaging protrusion 13a to engage the engaging protrusion 13a with the concave engaging section 1f.

The attachment and detachment ring 9 includes an outer circumference ring section 9B, an inner circumference pressing section 9A (a shaft fixing member), and a connecting section 9D. The outer circumference ring section 9B is movably supported in the outer circumferential portion of the box-shaped portion 1e in the axial direction. The inner circumference pressing section 9A is movably supported inside the box-shaped portion 1e in the axial direction. The connecting section 9D connects the outer circumference ring section 9B and the inner circumference pressing section 9A in the radial direction to interlock movement thereof.

The connecting section 9D passes through a through-hole (not shown) in a housing section constituting an outer circumferential portion of the box-shaped portion 1e.

The inner circumferential surface of the inner circumference pressing section 9A has a size that can cover at least the hook portion 13 in the circumferential direction. A position restricting surface 9a is formed to be spaced apart from the outer circumference side surface 1h outward in the radial direction by $H_1$. A length in the axial direction of the position restricting surface 9a is larger than a length obtained by adding an allowable moving amount of the input-side transmission shaft section 1A and a length of the hook portion 13 when the surgical instrument unit 1 is used.

A height $H_1$ of the position restricting surface 9a is set such that the hook portion 13 is sandwiched between the outer circumference side surfaces 1h and 2h and the position restricting surface 9a in a state in which engagement between the concave engaging section 1f and the engaging protrusion 13a is maintained, and the hook portion 13 is slidable in the axial direction. In the embodiment, the position restricting surface 9a is constituted such that a size in which the height in consideration of a manufacturing error or an assembly error of the hook portion 13 and the inner circumference pressing section 9A is added to $h_1$ so that the hook portion 13 is configured to be sandwiched therebetween with no gap.

In addition, the inner circumference pressing section 9A is capable of being moved between a position at which the shaft of the distal end side moving upon connection is engaged and fixed, and a released position, which is a position of the lowermost end side moving upon disconnection, or the like, in the axial direction, in order to fix the engagement state of the concave engaging section 1f and the hook portion 13.

In FIG. 3, the inner circumference pressing section 9A is disposed at a position at which it fixes a shaft in engagement with the shaft. In FIG. 5, the inner circumference pressing section 9A is disposed at the released position.

The engaging protrusion 9c (the shaft fixing member engaging section) is detachably engaged with the concave engaging section 1j of the connecting section 1B. The rod-shaped portion 9C having the engaging protrusion 9c extends from the end portion of the proximal end side of the inner circumference pressing section 9A toward the proximal end side.

The rod-shaped portion 9C is a portion having elasticity flexibly deformed in the radial direction. An inner circumferential side surface 9d inside in the radial direction of the rod-shaped portion 9C is aligned with the step-shaped protrusion section 1m of the connecting section 1B at the same height.

For this reason, when the inner circumference pressing section 9A is moved to the proximal end side, the engaging protrusion 9c comes into contact with the step-shaped protrusion section 1m, and the connecting section 1B is held down at the proximal end side. Accordingly, the connecting section 1B moves to the proximal end side together with the rod-shaped portion 9C to some extent. However, as shown in FIG. 5, when the connecting section 1B is further moved to arrive at a moving limit of the proximal end side, the rod-shaped portion 9C is flexibly deformed outward in the radial direction. Accordingly, the concave engaging section 1j is engaged with the engaging protrusion 9c.

The length of the rod-shaped portion 9C is set such that the position restricting surface 9a is retreated toward the proximal end side rather than the concave engaging section 1f, and the outside in the radial direction of the concave engaging section 1f is opened, in a state in which the engaging protrusion 9c is engaged with the concave engaging section 1j.

As shown in FIG. 6A, the attachment and detachment ring 9 according to the embodiment includes an inner circumference pressing section 9E constituting a part of the support body attachment and detachment mechanism unit 11B in a cross-section in which a position in the circumferential direction is different from that of a cross-section of FIG. 4. The inner circumference pressing section 9E will be described below in detail.

In the embodiment, as shown in FIG. 6A and FIG. 6B, the support body attachment and detachment mechanism unit 11B includes a concave engaging section 1s (a support body engaging section), a hook portion 16 (a support body connecting member), and an inner circumference pressing section 9E (a support body fixing member).

In addition, the support body attachment and detachment mechanism unit 11B may be disposed at the same cross-section as the cross-section on which the shaft attachment and detachment mechanism unit 11A is installed. In the embodiment, while the support body attachment and detachment mechanism unit 11B is disposed on the cross-section different from the cross-section on which the shaft attachment and detachment mechanism unit 11A is installed, for example, the cross-sectional view on which an angle is deviated in the circumferential direction.

The concave engaging section 1s is a support body engaging section configured to engage the intermediate member support body 2a with the surgical instrument unit support body 1a. As shown in FIG. 6B, the concave engaging section is formed on a step-shaped section 1q extending in the axial direction toward a bottom portion of a groove portion 1n formed at the distal end side of the surgical instrument unit support body 1a. In the embodiment, the concave engaging section 1s is constituted by a groove portion with a V-shaped cross-section in the axial direction.

An insertion guide section 1p is formed at the distal end side of the step-shaped section 1q. The insertion guide section 1p is formed parallel to the center axis $O_1$ to guide movement in an axial direction of an insertion section 2m protruding toward the proximal end portion of the intermediate member support body 2a.

A thickness in the radial direction of the insertion section 2m is equal to the height of the step-shaped section 1q from the insertion guide section 1p. For this reason, an outer circumference side surface 2k of the insertion section 2m and an upper surface 1r of the step-shaped section 1q are aligned in the engagement state shown in FIG. 6B.

In the embodiment, when the hook portion 16 (to be described below) is in engagement, in the axial direction, the concave engaging section is formed in a position in which a distal end surface 1t of the step-shaped section 1q comes into contact with a proximal end surface 2 of the insertion section 2m of the intermediate member support body 2a. However, according to conditions of a shape or strength of the hook portion 16, when there is no obstruction in engagement force, the concave engaging section is formed in a position in which the distal end surface 1t is engaged with the proximal end surface 2i in a state that the distal end surface 1t is spaced apart from the proximal end surface 2i.

The hook portion 16 is a rod-shaped member having a width that is capable of being engaged with the concave engaging section 1s, for example, a width in the depth direction of FIG. 6B. The hook portion 16 has one end side pivotally fixed to the insertion section 2m of the intermediate member support body 2a via a hinge portion 16d, and is disposed on the outer circumference side surface 2k of the insertion section 2m. However, a pivot range of the hook portion 16 may be a small angle range such that an engaging protrusion 16a (described below) is moved to a position substantially equal to the outer circumference side surface 2k.

In addition, the hinge portion 16d may include, for example, an elastic member or a spring, and may be configured such that the hook portion 16 is biased in a direction to be in close contact with the outer circumference side surface 2k.

The hook portion 16 has a length such that the other end portion protrudes toward the proximal end side rather than the proximal end surface 2j, in a posture parallel to the insertion section 2m shown in FIG. 6B. An engaging protrusion 16a (a support body connection engaging section) having an angular section engaged with the concave engaging section 1s is formed at the other end portion inside in the radial direction.

The engaging protrusion 16a is formed at a position that is capable of being completely engaged with the concave engaging section 1f in a state in which the distal end surface 1t comes into contact with the proximal end surface 2j, and the upper surface 1r and the outer circumference side surface 2k are aligned with each other.

In addition, in the hook portion 16, a thickness of the intermediate section, excluding the engaging protrusion 16a and the hinge portion 16d, is $h_2$. For this reason, in the engagement state shown in FIG. 6B, an outer circumferential surface 16b of the hook portion 16 has a flat surface protruding outward from the upper surface 1r and the outer circumference side surface 2k in the radial direction by a height $h_2$.

Further, a taper 16c inclined from one end side of the outer circumferential surface 16b toward the other end is formed at a rear side of the engaging protrusion 16a in the other end side of the engaging protrusion 16a. Even in a position in which the distal end surface 1t abuts the proximal end surface 2j, according to disturbance of gravity, or the like, the engaging protrusion 16a may not be engaged with the concave engaging section 1f. In this case, the inner circumference pressing section 9E can contact the taper 16c to hold down the engaging protrusion 16a to engage the engaging protrusion 16a with the concave engaging section 1f.

The inner circumferential surface of the inner circumference pressing section 9E has a size that can cover at least the hook portion 16 in the circumferential direction. The inner circumferential surface of the inner circumference pressing section 9E has a position restricting surface 9b spaced apart from the upper surface 1r outward in the radial direction by $H_2$. A length in the axial direction of the position restricting surface 9b is a length that the hook portion 16 is capable of being held down from the outside in the radial direction when the attachment and detachment ring 9 moves to a shaft engagement fixing position (a first state).

The hook portion 16 does not move in the axial direction when the engagement state is fixed. For this reason, the length in the axial direction of the position restricting surface 9b may be shorter than the entire length of the hook portion 16.

The height $H_2$ of the position restricting surface 9b is set such that the hook portion 16 is sandwiched between the upper surface 1r, the outer circumference side surface 2k and the position restricting surface 9a in a state in which the engagement between the concave engaging section 1s and the engaging protrusion 16a is maintained, and the hook portion 16 is slidable in the axial direction. In the embodiment, the height of the position restricting surface 9b is set in consideration of a manufacturing error or an assembly error of the hook portion 16 and the inner circumference pressing section 9E is added to $h_2$, and the hook portion 16 is configured to be sandwiched therebetween with no gap.

As described above, the support body attachment and detachment mechanism unit 11B is accommodated in the groove portion 1n upon mounting of the embodiment. That is to say, the embodiment is an example that the support body attachment and detachment mechanism unit 11B is installed inside the surgical instrument unit support body 1a and the intermediate member support body 2a.

Next, an operation of the operation support device 50 having the above-mentioned configuration will be described focusing on the attachment and detachment method.

The surgical instrument unit 1, the intermediate member 2, and the surgical instrument drive unit 3 are connected to each other. That is, as shown in FIG. 2A, FIG. 2B and FIG. 3, first, in the intermediate member insertion hole 3c of the surgical instrument drive unit 3, the cylindrical section 2B of the intermediate member 2 is inserted from the proximal end side of the surgical instrument drive unit 3, and a connecting body of the surgical instrument drive unit 3 and the intermediate member 2 is formed.

Once the surgical instrument drive unit 3 and the intermediate member 2 are connected to each other, in principle, the connection state is not released during the operation. For this reason, even when attachment and detachment is time-consuming, there is no time loss during the operation. Here, the shaft attachment and detachment mechanism unit 12A and a support body attachment and detachment mechanism unit 12B according to the embodiment employ well-known mechanisms.

In the shaft attachment and detachment mechanism unit 12A and the support body attachment and detachment mechanism unit 12B, first, in a state in which each of the drive force transmission shafts 3b protrudes from the connecting end portion $C_{32}$ of the surgical instrument drive unit 3, the intermediate member 2 is inserted into the intermediate member insertion hole 3c of the surgical instrument drive unit 3 from the proximal end side. The shaft engaging section 2e and the shaft engaging section 3d are engaged with each other, and thus, the connecting end portion $C_{23}$ comes into contact with the connecting end portion $C_{32}$. Here, the drape ring 6 is fitted into the distal end side of the intermediate member support body 2a of the intermediate member 2.

Next, the intermediate member support body 2a and the surgical instrument drive unit support body 3a are engaged with and fixed to each other by using the fixing ring 14.

Accordingly, since the distal end portion of the cylindrical section 2B of the intermediate member 2 is exposed to the distal end side of the surgical instrument drive unit 3, the drape ring 8 is fitted onto and fixed to the outer circumference of distal end portion of the cylindrical section 2B.

In this way, when the intermediate member 2 and the surgical instrument drive unit 3 are connected to each other, as shown in FIG. 3, the surgical instrument drive unit 3 is surrounded by the surface 7a of the drape 7. Then, the surgical instrument unit insertion hole 2d of the intermediate member 2 constitutes a through-hole together with two through-holes which are formed in the drape 7, i.e., inner circumferential portions of the drape rings 6 and 8. That is, a surface of the surgical instrument unit insertion hole 2d of the intermediate member 2 is connected to the surface 7b of the drape 7. As described above, the first region $A_U$ and the second region $A_U$ are bounded by the drape 7 and the intermediate member 2. The inside of the surgical instrument unit insertion hole 2d is constituted by the second region $A_C$.

Next, the operation unit 1c and the cylindrical portion 1d of the surgical instrument unit 1 are inserted from the proximal end side of the surgical instrument unit insertion hole 2d of the intermediate member 2 connected to the surgical instrument drive unit 3, and a connecting body of the intermediate member 2 and the surgical instrument unit 1 is formed.

Since the surgical instrument unit 1 is sterilized, these connecting operations should be performed in a place in a sterilized state, for example, an operating room, or the like. In addition, the surgical instrument unit 1 may be exchanged with a new one in the operating room according to necessity in the operation or a patient during the operation.

Here, in the embodiment, the configuration of the shaft attachment and detachment mechanism unit 11A and the support body attachment and detachment mechanism unit 11B is employed such that the attachment and detachment is capable of being rapidly and easily performed.

Hereinafter, first, an attachment and detachment method of the shaft attachment and detachment mechanism unit 11A and the support body attachment and detachment mechanism unit 11B will be described, and then a motion of the entire attachment and detachment will be described.

A motion of attaching and detaching the shaft attachment and detachment mechanism unit 11A will be described together with the attachment and detachment method thereof.

Figure 7A:
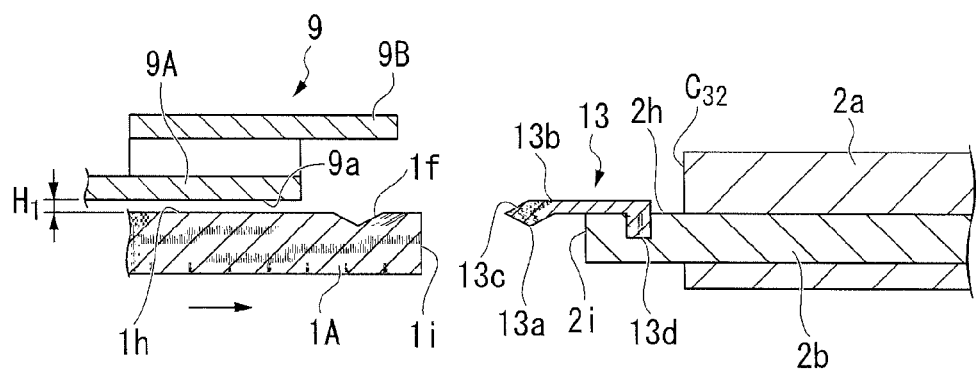
FIG. 7A is a view for schematically describing a motion in which an intermediate shaft section and a surgical instrument unit shaft section are engaged with each other in the operation support device according to the first embodiment of the invention.

FIG. 7A, FIG. 7B, FIG. 7C and FIG. 7D are views for schematically describing a motion in which the intermediate shaft section and the surgical instrument unit shaft section of the operation support device according to the first embodiment of the invention are engaged with each other. FIG. 8A and FIG. 8B are views for schematically describing a motion when the intermediate shaft section and the surgical instrument unit shaft section of the operation support device according to the first embodiment of the invention are engaged with each other. FIG. 9A, FIG. 9B, FIG. 9C and FIG. 9D are views for schematically describing a motion in which the intermediate member support body and surgical instrument unit support body of the operation support device according to the first embodiment of the invention are engaged with each other.

In the attachment and detachment method of the invention, while mounting, a shaft engagement process for engagement of the shaft and a shaft engagement fixing process for fixing the engagement of the shaft are sequentially performed. When the mounting is released, a shaft engagement fixing release process of releasing the engagement fixing of the shaft and a shaft engagement release process of releasing the engagement of the shaft are sequentially performed.

The shaft engagement process is a process of approaching the intermediate member support body 2a, which is a first support body, and the surgical instrument unit support body 1a, which is a second support body, each other in the moving direction of the intermediate shaft 2b and the input-side transmission shaft section 1A, and engaging the concave engaging section 1f with the engaging protrusion 13a.

An operator makes the surgical instrument unit support body 1a, which is the second support body interlocked with the attachment and detachment ring 9, approach the intermediate member support body 2a, which is the first support body, while holding the attachment and detachment ring 9. At that time, the intermediate member 2 having the intermediate member support body 2a, which is the first support body, and the surgical instrument drive unit 3 connected to the intermediate member 2 are held by an arm (not shown) and fixed thereto.

The intermediate member support body 2a and the surgical instrument unit support body 1a have a positioning portion (not shown) configured to perform mutual positioning in the circumferential direction. After performing a position by using the positioning portion, the surgical instrument unit support body 1a is inserted into the intermediate member support body 2a. Accordingly, as shown in FIG. 7A, the proximal end surface 2i of each of the intermediate shafts 2b and the distal end surface 1i of each of the driving force transmission members 1b approach each other by little and little in an opposite state.

At this time, the inner circumference pressing section 9A of the attachment and detachment ring 9 is moved together with the surgical instrument unit support body 1a in a state in which the inner circumference pressing section 9A is disposed at the released position in the surgical instrument unit 1. For this reason, the concave engaging section 1f is opened upward.

Figure 7B:
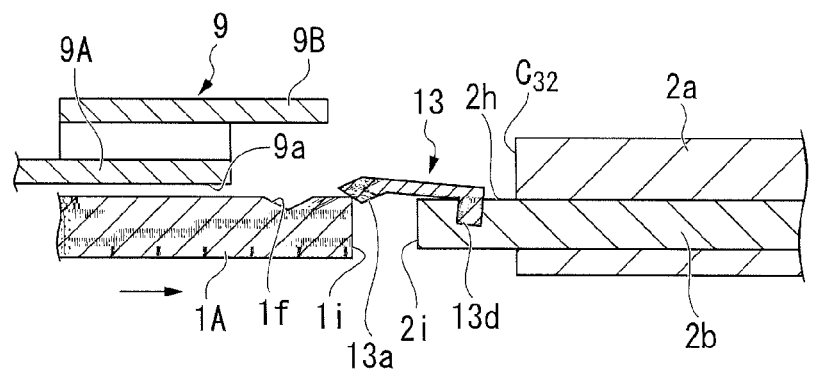
FIG. 7B is a view for schematically describing a motion in which the intermediate shaft section and the surgical instrument unit shaft section are engaged with each other in the operation support device according to the first embodiment of the invention.
Figure 8A:
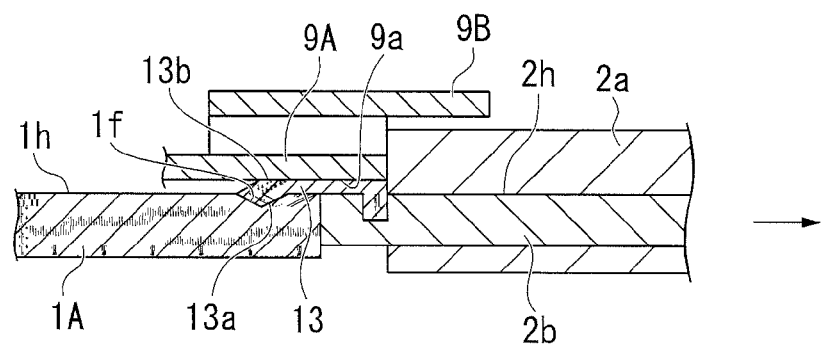
FIG. 8A is a view for schematically describing a motion when the intermediate shaft section and the surgical instrument unit shaft section are engaged with each other in the operation support device according to the first embodiment of the invention.
Figure 8B:
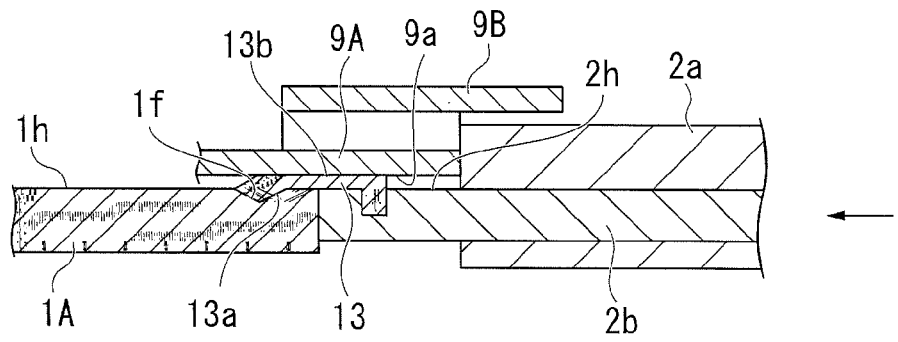
FIG. 8B is a view for schematically describing a motion when the intermediate shaft section and the surgical instrument unit shaft section are engaged with each other in the operation support device according to the first embodiment of the invention.

As shown in FIG. 7B, when a distance between the distal end surface 1i and the proximal end surface 2i is reduced, the distal end portion of the input-side transmission shaft section 1A comes into contact with the engaging protrusion 13a of the hook portion 13 to pivot the hook portion 13.

Further, when the mutual distance is reduced, the engaging protrusion 13a moves forward while being pushed up onto the outer circumference side surface 1h.

Figure 7C:
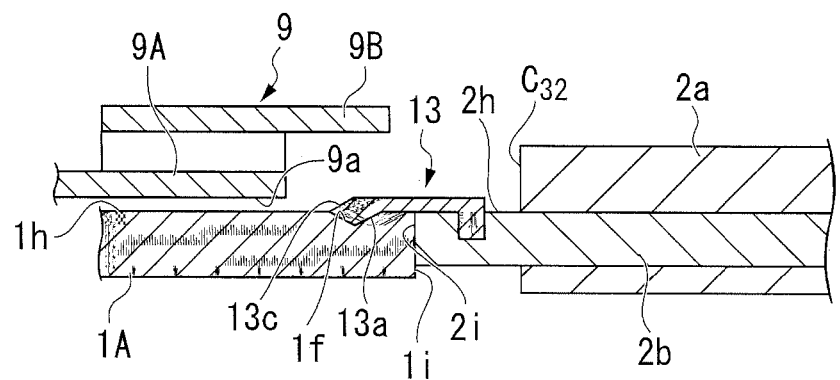
FIG. 7C is a view for schematically describing a motion in which the intermediate shaft section and the surgical instrument unit shaft section are engaged with each other in the operation support device according to the first embodiment of the invention.

As shown in FIG. 7C, when the engaging protrusion 13a is disposed on the concave engaging section 1f and gravity acts on the hook portion 13 in a downward direction of FIG. 7C, the engaging protrusion 13a enters the concave engaging section 1f, and the engaging protrusion 13a is engaged with the concave engaging section 1f. When gravity acts on the hook portion 13 in an upward direction of FIG. 7C, the engaging protrusion 13a does not enter the concave engaging section 1f. In this case, as described below, engagement between the concave engaging section 1f and the engaging protrusion 13a is performed in the next process.

As described above, the shaft engagement process is terminated.

In addition, in the process, while the engaging protrusion 13a may be completely inserted into the concave engaging section 1f and engaged therewith, as in the embodiment, the concave engaging section 1f may only partially enter the engaging protrusion 13a. That is, in the process, when the concave engaging section 1f and the engaging protrusion 13a are to be spaced apart from each other in the axial direction, they are considered to be engaged as long as they are in contact with each other to generate a resistance against the separation motion. However, in the engagement state, when an external force for separation is increased to some extent, the engagement state is released.

Further, this engagement state is formed even before the distal end surface 1i comes into connect with the proximal end surface 2i.

In addition, when the hinge portion 13d is constituted to bias the hook portion 13 to the outer circumference side surface 2h, in the process, the engaging protrusion 13a may more securely enter the concave engaging section 1f to enhance the engagement state.

Next, the shaft engagement fixing process is performed. The shaft engagement fixing process is a process in which the shaft that maintains the engagement with the concave engaging section 1f forms the engagement-fixed state, by moving the inner circumference pressing section 9A, which is a shaft fixing member, to hold down the hook portion 13. However, the process is capable of being performed continuously after the above-mentioned shaft engagement process. That is, an operator brings the surgical instrument unit support body 1a, which is the second support body interlocked with the attachment and detachment ring 9, in contact with the intermediate member support body 2a, which is the first support body, while holding the attachment and detachment ring 9. Then, while the surgical instrument unit support body 1a is not moved with respect to the intermediate member support body 2a, the attachment and detachment ring 9 moves toward the connecting end portion $C_{32}$ on the surgical instrument unit support body 1a.

Figure 7D:
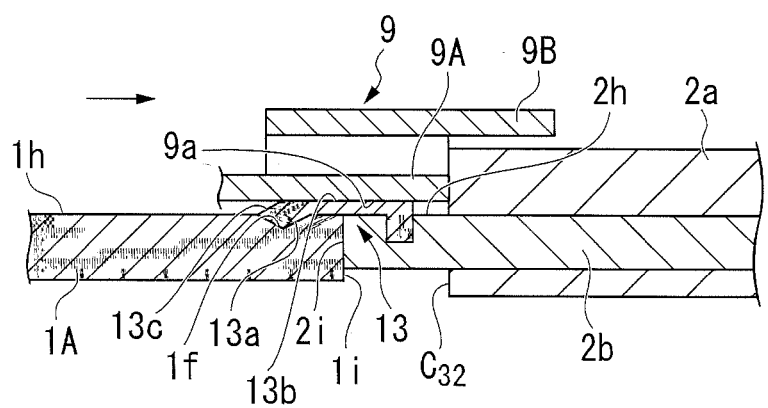
FIG. 7D is a view for schematically describing a motion in which the intermediate shaft section and the surgical instrument unit shaft section are engaged with each other in the operation support device according to the first embodiment of the invention.

That is, as shown in FIG. 7D, the inner circumference pressing section 9A is moved toward the hook portion 13 in the axial direction. In the embodiment, the outer circumference ring section 9B of the attachment and detachment ring 9 is slidably moved toward a shaft engagement fixing position in the axial direction. Accordingly, the inner circumference pressing section 9A connected to the outer circumference ring section 9B is moved.

At this time, even when the hook portion 13 is in the engagement state to be floated from the outer circumference side surface 1h in the previous process, by the distal end portion of the inner circumference pressing section 9A coming into contact with the taper 13c, a force of holding down the hook portion 13 toward the outer circumference side surface 1h is applied. For this reason, the hook portion 13 is capable of being held down toward the outer circumference side surface 1h, and the entire engaging protrusion 13a is capable of being fitted into the concave engaging section 1f.

As described above, when the inner circumference pressing section 9A is pushed onto the outer circumferential surface 13b of the hook portion 13, the hook portion 13 is sandwiched between the outer circumference side surfaces 1h and 2h and the position restricting surface 9a and held down from the outside in the radial direction. As a result, separation of the engaging protrusion 13a from the concave engaging section 1f and release of the engagement is capable of being prevented. That is, the first state in which the shaft engagement state is maintained is formed.

As described above, the shaft engagement fixing process is terminated.

In addition, the hook portion 13 by holding down the position restricting surface 9a means that the hook portion 13 is positionally restricted in the radial direction within a range in which the engagement is not released by moving the hook portion 13 in radial direction. For this reason, there is no need to keep the position restricting surface 9a in contact with the outer circumferential surface 13b.

In this way, the intermediate shaft 2b and the input-side transmission shaft section 1A are integrally engaged with each other via the hook portion 13. In the embodiment, since a distance between the position restricting surface 9a and the outer circumference side surface 1h is $H_1$, the hook portion 13 is capable of being slidably moved with respect to the position restricting surface 9a in the axial direction.

For this reason, when the driving force is transmitted from the surgical instrument drive unit 3 to the intermediate shaft 2b, as shown in FIG. 8A and FIG. 8B, the hook portion 13 and the input-side transmission shaft section 1A engaged with the hook portion 13 move together with the intermediate shaft 2b to advance and retreat in the axial direction. The position restricting surface 9a also serves as a movable guide configured to guide the movement of the driving force transmission member 1b and the intermediate shaft 2b via the hook portion 13.

Since a gap between the position restricting surface 9a and the outer circumference side surfaces 1h and 2h is a constant value $H_1$, the engaging protrusion 13a is not spaced apart from the concave engaging section 1f in the radial direction during movement. For this reason, even when the force of separating the driving force transmission member 1b and the surgical instrument unit support body 1a from each other in the axial direction is applied, the engagement state of the shafts of the driving force transmission member 1b and the intermediate member support body 2a is maintained.

A length in the axial direction of the position restricting surface 9a is a length larger than a length in which an allowable moving amount of the input-side transmission shaft section 1A is added to a length of the hook portion 13 when the surgical instrument unit 1 is used. For this reason, the first state is capable of being formed in the entire moving range in which the hook portion 13 moves.

Next, when the shaft is released from the engagement-fixed state, the shaft engagement fixing release process and the shaft engagement release process may be performed in the above-mentioned sequence.

The shaft engagement fixing release process is a process for forming the second state in which releasing a holding down to the connection engaging section by moving the shaft fixing member from a position of the first state.

The shaft engagement release process is a process for releasing the engagement between the first shaft section and the second shaft section by spacing between the first support body and the second support body from each other in the moving direction of the first shaft section and the second shaft section.

Specifically, since the shaft engagement fixing process and the shaft engagement process may be performed in a sequence opposite to the above-mentioned sequence, the description is omitted.

In the attachment and detachment motion of the support body attachment and detachment mechanism unit 11B, an attachment and detachment method for the support body attachment and detachment mechanism unit 11B will be described with reference to FIG. 9A, FIG. 9B, FIG. 9C and FIG. 9D.

In the method, when the support body attachment and detachment mechanism unit 11B is mounted, the support body engagement process and the support body engagement fixing process are sequentially performed. When the mounting of the support body attachment and detachment mechanism unit 11B is released, the support body engagement fixing release process and the support body engagement release process are sequentially performed.

In the embodiment, these processes are performed in parallel with the attachment and detachment motion of the above-mentioned shaft attachment and detachment mechanism unit 11A, because the inner circumference pressing section 9A and the inner circumference pressing section 9E are interlocked and moved by the outer circumference ring section 9B.

The attachment and detachment motion of the support body attachment and detachment mechanism unit 11B becomes the same as when the concave engaging section 1f, the hook portion 13 and the inner circumference pressing section 9A are replaced with the concave engaging section 1s, the hook portion 16 and the inner circumference pressing section 9E, respectively, in the attachment and detachment motion of the shaft attachment and detachment mechanism unit 11A.

The support body engagement process is a process of approaching the intermediate member support body 2a and the surgical instrument unit support body 1a each other in the moving direction of the intermediate shaft 2b and the input-side transmission shaft section 1A to engage the concave engaging section is with the engaging protrusion 16a.

Figure 9A:
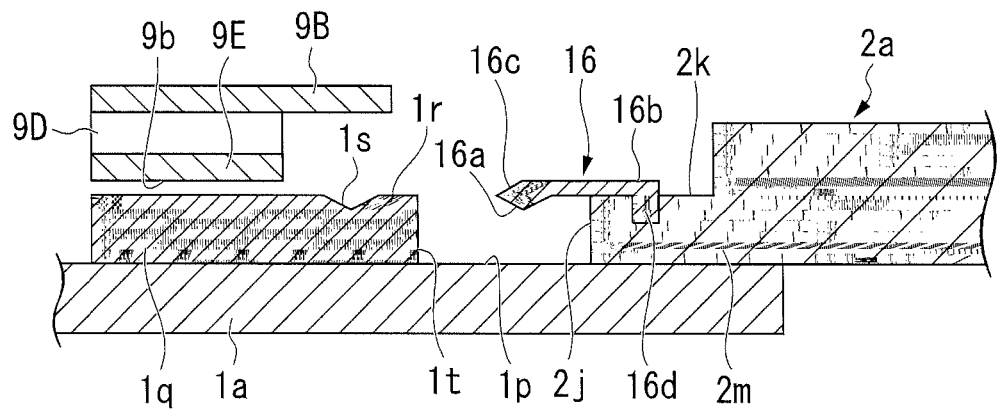
FIG. 9A is a view for schematically describing a motion in which an intermediate member support body and a surgical instrument unit support body are engaged with each other in the operation support device according to the first embodiment of the invention.

As shown in FIG. 9A, according to relative movement of the surgical instrument unit support body 1a and the intermediate member support body 2a caused by the mounting motion of the shaft attachment and detachment mechanism unit 11A, the distal end surface 1t of each of the step-shaped sections 1q and the proximal end surface 2j of each of the insertion sections 2m gradually approach each other in an opposite state.

At this time, similar to the inner circumference pressing section 9A disposed at the released position, the inner circumference pressing section 9E moves with the surgical instrument unit support body 1a in a state disposed at the proximal end side. For this reason, the concave engaging section 1s is opened upward.

Figure 9B:
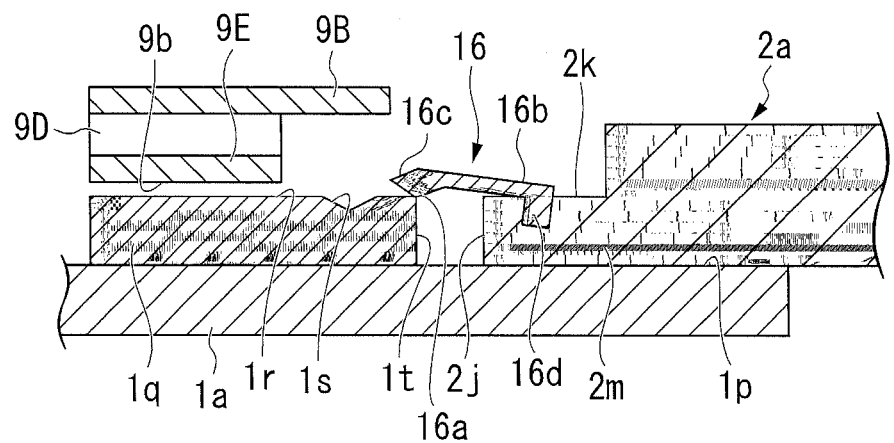
FIG. 9B is a view for schematically describing a motion in which an intermediate member support body and a surgical instrument unit support body are engaged with each other in the operation support device according to the first embodiment of the invention.

As shown in FIG. 9B, when a distance between the distal end surface 1t and the proximal end surface 2j is reduced, the distal end portion of the step-shaped section 1q comes into contact with the engaging protrusion 16a of the hook portion 16 to pivot the hook portion 16. When the distance therebetween is further reduced, the engaging protrusion 16a is pushed up onto the upper surface 1r and moves forward.

Figure 9C:
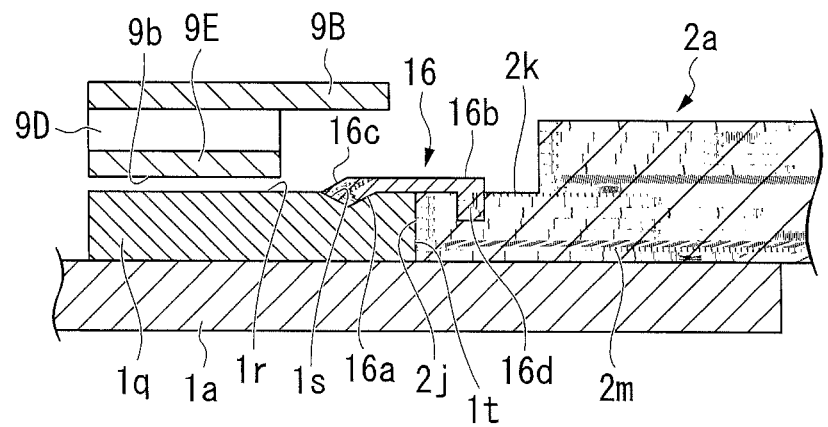
FIG. 9C is a view for schematically describing a motion in which an intermediate member support body and a surgical instrument unit support body are engaged with each other in the operation support device according to the first embodiment of the invention.

As shown in FIG. 9C, when the engaging protrusion 16a is disposed on the concave engaging section 1s, the engaging protrusion 16a enters the concave engaging section 1s, and the engaging protrusion 16a is engaged with the concave engaging section 1s.

As described above, the support body engagement process is terminated.

In addition, in the process, it is possible to engage the support body in the same state as the shaft engagement process. Further, when the hinge portion 16d biases the hook portion 16 to the outer circumference side surface 2k, in the process, the engaging protrusion 16a may more securely enter the concave engaging section 1s to enhance the engagement state.

Next, the support body engagement fixing process is performed. The process is a process to form the engagement fixing state which maintain the engagement state between the support body and the concave engaging section 1s, by moving the inner circumference pressing section 9E, which is a support body fixing member, to hold down the hook portion 16.

Figure 9D:
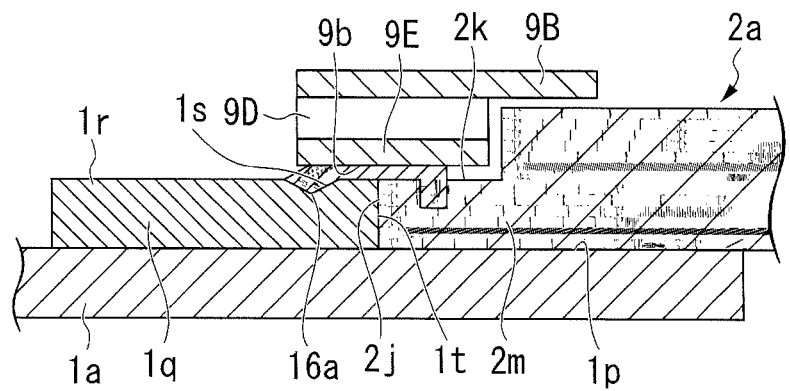
FIG. 9D is a view for schematically describing a motion in which an intermediate member support body and a surgical instrument unit support body are engaged with each other in the operation support device according to the first embodiment of the invention.

In the process, as shown in FIG. 9D, the inner circumference pressing section 9E is moved toward the hook portion 16 in the axial direction. However, in the embodiment, since the inner circumference pressing section 9E is engaged with the outer circumference ring section 9B, the shaft engagement fixing process is initiated and simultaneously the process is also performed.

In the process, even when the engagement state in the previous process is in an imperfect engagement state and the hook portion 16 is in an engagement state without support from the outer circumference side surface 2k, the distal end portion of the inner circumference pressing section 9E comes into contact with the taper 16c. Accordingly, a force of holding down the hook portion 16 toward the outer circumference side surface 2k is applied. For this reason, the hook portion 16 is held down toward the outer circumference side surface 2k, and the entire engaging protrusion 16a is fitted into the concave engaging section 1s.

As described above, when the inner circumference pressing section 9E is pushed onto the outer circumferential surface 16b of the hook portion 16, the hook portion 16 is sandwiched between the upper surface 1r, the outer circumference side surface 2k and the position restricting surface 9b to be held down from the outside in the radial direction. As a result, it is possible to prevent the engagement fixing state from releasing that the engaging protrusion 16a is separated from the concave engaging section 1s. That is, the support body engagement state is maintained. And a third state is formed.

As described above, the support body engagement fixing process is terminated.

In this way, the intermediate member support body 2a and the surgical instrument unit support body 1a are integrally engaged with each other via the hook portion 16.

In addition, the outer circumference ring section 9B and the intermediate member support body 2a may be fixed to a position of FIG. 9D by snap fitting (not shown). Accordingly, when the intermediate shaft 2b and the input-side transmission shaft section 1A are engaged and moved as shown in FIG. 8A and FIG. 8B, it is possible to more securely prevent the outer circumference ring section 9B from being moved by a frictional force generated between the position restricting surface 9a and the outer circumferential surface 13b of the hook portion 13.

Next, to release the third state, the support body engagement fixing release process and the support body engagement release process may be sequentially performed.

The support body engagement fixing release process is a process of forming a fourth state in which the engagement of the support is released by moving the support body fixing member from a position of the third state to release holding down to the support body connection engaging section.

The support body engagement release process is a process of releasing the engagement between the first support body and the second support body by separating the first support body and the second support body from each other in the moving direction of the first shaft section and the second shaft section.

Specifically, since the support body engagement fixing process and the support body engagement process may be performed in a sequence opposite to the above-mentioned sequence, the description is omitted.

Next, the entire attachment and detachment motion will be described focusing on an operation in which the processes are performed in parallel.

However, in the following description, in order to easily understand the entire attachment and detachment motion, an example in which the shaft attachment and detachment mechanism unit 11A and the support body attachment and detachment mechanism unit 11B are each provided in a pair on the same cross-sectional surface will be described. Here, since the drawings are complicated when the specific configuration is described, the support body attachment and detachment mechanism unit 11B will be described with reference to the drawings of the configuration of the modified example.

Figure 10:
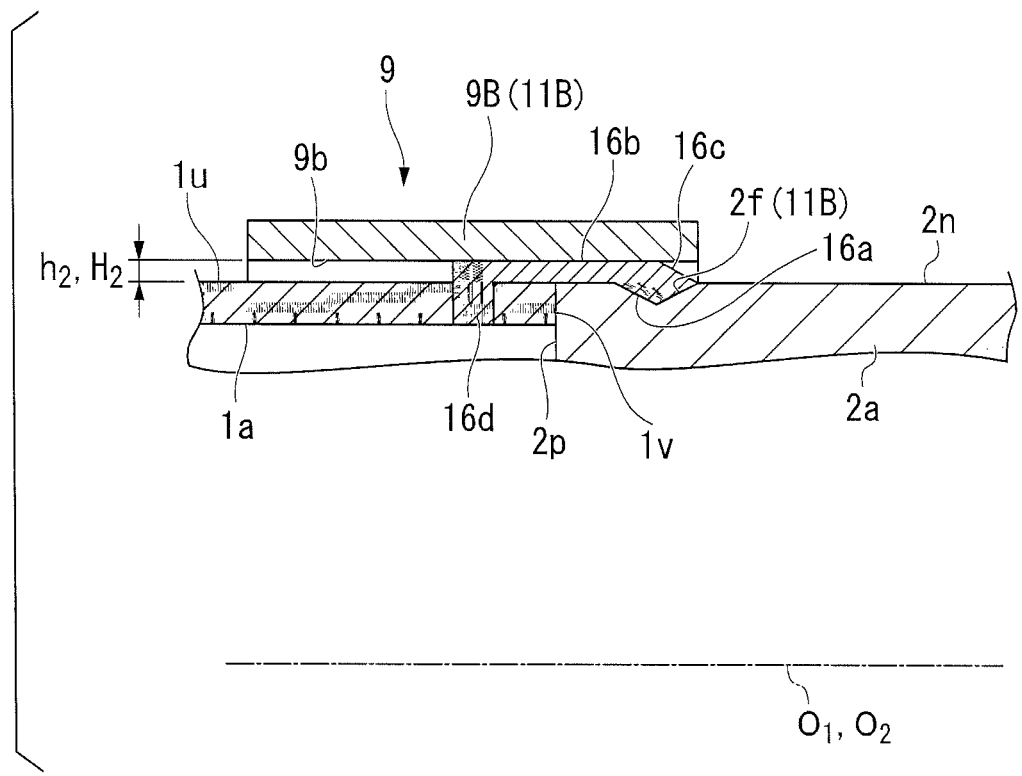
FIG. 10 is a schematic cross-sectional view showing a modified example of major parts of a support body attachment and detachment mechanism unit of the operation support device according to the first embodiment of the invention.
Figure 11A:
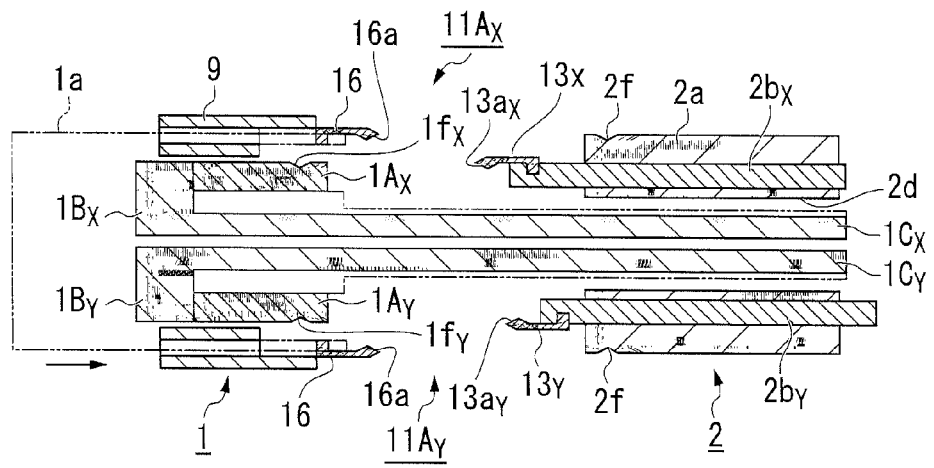
FIG. 11A is a view for schematically describing a motion in which the surgical instrument unit is mounted on the intermediate member of the operation support device according to the first embodiment of the invention.
Figure 11B:
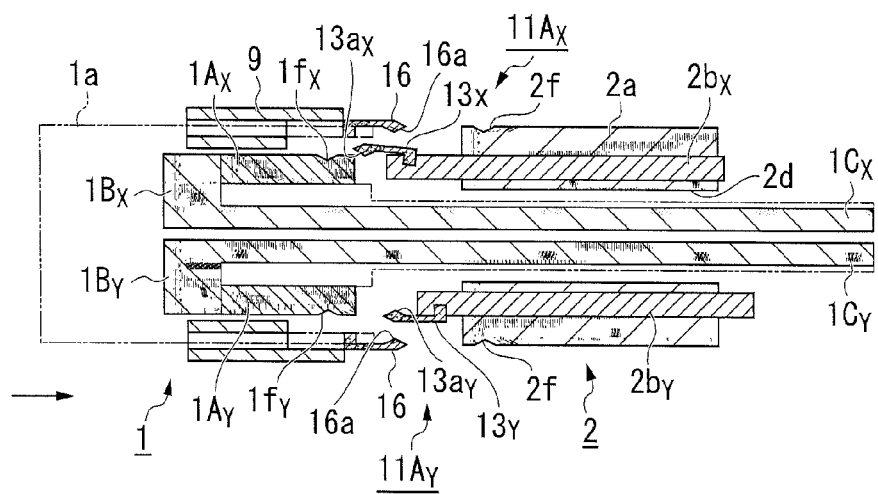
FIG. 11B is a view for schematically describing a motion in which the surgical instrument unit is mounted on the intermediate member of the operation support device according to the first embodiment of the invention.
Figure 11C:
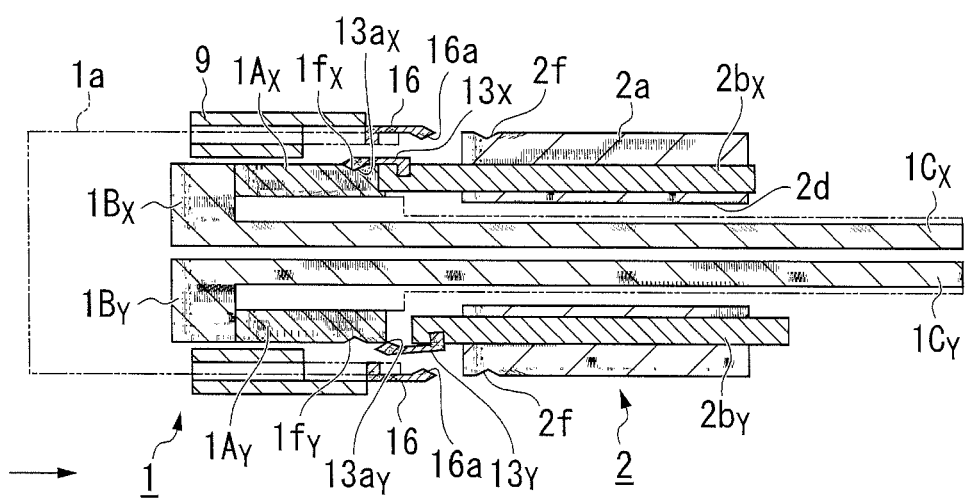
FIG. 11C is a view for schematically describing a motion in which the surgical instrument unit is mounted on the intermediate member of the operation support device according to the first embodiment of the invention.
Figure 12A:
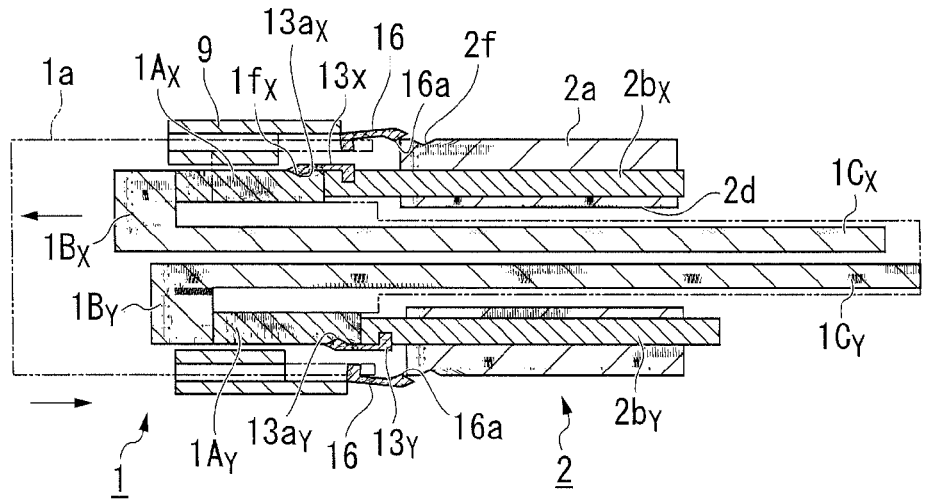
FIG. 12A is a view for describing a motion continued from FIG. 11A to FIG. 11C.
Figure 12B:
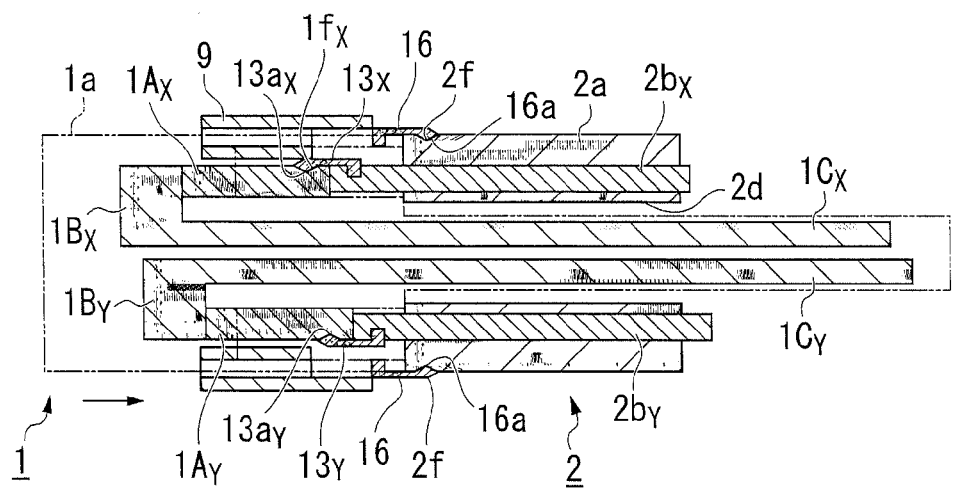
FIG. 12B is a view for describing a motion continued from FIG. 12A.
Figure 12C:
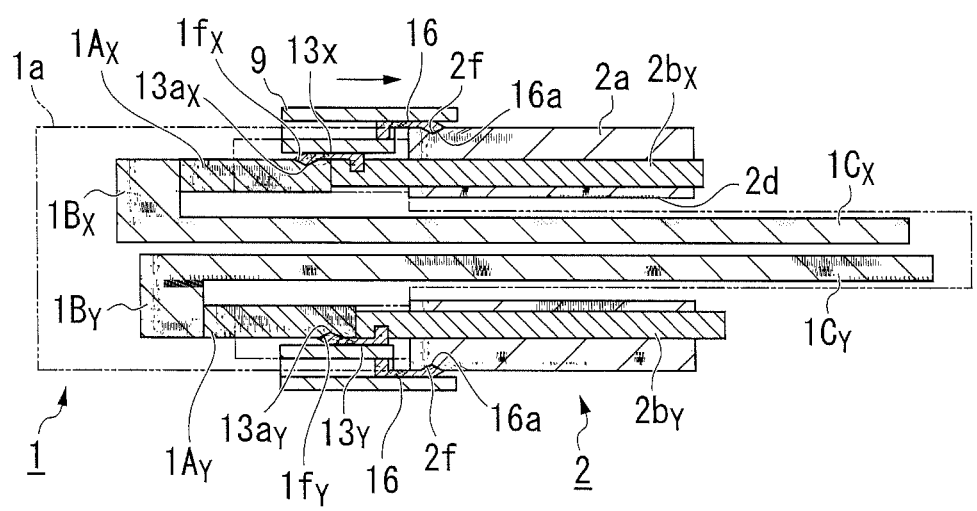
FIG. 12C is a view for describing a motion continued from FIG. 12A.

FIG. 10 is a schematic cross-sectional view showing a modified example of major parts of the support body attachment and detachment mechanism unit of the operation support device according to the first embodiment of the invention. FIG. 11A, FIG. 11B and FIG. 11C are views for schematically describing a connecting motion of the surgical instrument unit with respect to the intermediate member of the operation support device according to the first embodiment of the invention. FIG. 12A, FIG. 12B and FIG. 12C describe a motion continued from FIG. 11C. FIG. 13A, FIG. 13B, FIG. 13C and FIG. 13D are schematically describing an engagement operation of the shaft fixing member and the second shaft engaging section of the operation support device according to the first embodiment of the invention.

First, a configuration of a modified example of the support body attachment and detachment mechanism unit 11B will be described in brief.

As shown in FIG. 10, in the modified example, the hook portion 16 is formed at the outer circumferential portion of the surgical instrument unit support body 1a. A concave engaging section 2f engaged with the engaging protrusion 16a at the outer circumferential portion of the intermediate member support body 2a is formed at an outer circumference side surface 2n of the intermediate shaft 2b. The position restricting surface 9b is formed at a rear surface side of the outer circumference ring section 9B. The position restricting surface $9b$ is formed at a position of a height $H_Z$ from an outer circumferential surface $1u$ of the surgical instrument unit support body $1a$ at which the hook portion 16 is formed.

The surgical instrument unit support body $1a$ and the intermediate member support body $2a$ have a distal end surface $1v$ of the surgical instrument unit support body $1a$ and a proximal end surface $2p$ of the intermediate member support body $2a$ coming into contact with each other in the engagement state.

In the above-mentioned configuration of the modified example, in the support body engagement process, the surgical instrument unit support body $1a$ and the intermediate member support body $2a$ are relatively moved in the axial direction and the distal end surface $1v$ and the proximal end surface $2p$ approach each other. Accordingly, the engaging protrusion $16a$ of the hook portion 16 is pushed onto the intermediate member support body $2a$ so as to be engaged with the concave engaging section $2f$.

In the support body engagement fixing process, by the outer circumference ring section 9B being moved toward the distal end side, the hook portion 16 is held down toward the outer circumferential surface $1u$ side. As a result, the hook portion 16 is sandwiched between the position restricting surface $9b$ and the intermediate member support body $2a$, and then, a third state, in which engagement of the support body is fixed, is formed.

As described above, even in the configuration in which the support body connecting member is installed at the second support body and the support body engaging section is installed at the first support body, similar to the first embodiment, by the support bodies being moved in the axial direction and the support body fixing member being moved in the axial direction, engagements of the support bodies are capable of being performed.

In the embodiment and modified example, the support body attachment and detachment mechanism unit 11B is installed at the intermediate member support body $2a$ and the surgical instrument unit support body $1a$, and the attachment and detachment ring 9 used in the support body attachment and detachment mechanism unit 11B is one. Even when the plurality of support body attachment and detachment mechanism units 11B having the same configuration are installed, the motions are the same.

On the other hand, when the plurality of shaft attachment and detachment mechanism units 11A are installed, stopping positions in the axial direction of the drive force transmission shafts $3b$ may differ according to circumstances under which the surgical instrument drive unit 3 has stopped upon attachment and detachment.

For example, as shown in FIG. 11A, two kinds of shaft attachment and detachment mechanism units $11A_X$ and $11A_Y$ are considered. Since motions of the two kinds of shaft attachment and detachment mechanism units $11A_X$ and $11A_Y$ will be separately described, subscripts X and Y are added to reference numerals of the configuration members.

For example, the intermediate shaft $2b_X$ belonging to the shaft attachment and detachment mechanism unit $11A_X$ may protrude toward the proximal end side and stop, rather than the intermediate shaft $2b_Y$ belonging to the shaft attachment and detachment mechanism unit $11A_Y$.

In this case, according to the conventional art, the intermediate shafts $2b_X$ and $2b_Y$ have different engagement positions in the axial direction. For this reason, a task of matching protrusion amounts of the intermediate shafts $2b_X$ and $2b_Y$, i.e., initialization of positions for attachment and detachment of the shaft attachment and detachment mechanism unit 11A, is needed. When the initialization of the positions is not performed, the positions of the input-side transmission shaft section $1A_X$ and $1A_Y$ are aligned with the protrusion positions of the intermediate shaft $2b_X$ and $2b_Y$, and the engagement tasks are needed. In any case, the attachment and detachment tasks are complicated.

In the embodiment, since the attachment and detachment motion is performed as described below, the attachment and detachment is easily performed even in this case.

Hereinafter, an example in which the intermediate member 2 is fixed and the surgical instrument unit 1 is inserted will be described.

When the surgical instrument unit 1 is inserted into the surgical instrument unit insertion hole $2d$ to approach the intermediate member 2 in the axial direction, as shown in FIG. 11B, the hook portion $13_X$ comes into contact with a distal end of the input-side transmission shaft section $1A_X$ (corresponding to a state of FIG. 7B). At this time, the hook portion $13_Y$ is spaced apart from the input-side transmission shaft section $1A_Y$ (corresponding to a state of FIG. 7A).

At this time, as shown in FIG. 5 (not shown in FIG. 11A), the engaging protrusions $9c_X$ and $9c_Y$ of the rod-shaped portions $9C_X$ and $9C_Y$ are engaged with the concave engaging sections $1j_X$ and $1j_Y$ of the connecting sections $1B_X$ and $1B_Y$.

When the surgical instrument unit 1 is further inserted into the surgical instrument unit insertion hole $2d$, as shown in FIG. 11C, the engaging protrusion $13a_X$ is engaged with the concave engaging section $1f_X$ (corresponding to a state of FIG. 7C). The hook portion $13_Y$ comes into contact with a distal end of the input-side transmission shaft section $1A_Y$ (corresponding to a state of FIG. 7B).

At this time, since the hook portion 16 does not come into contact with the intermediate member support body $2a$, the support body engagement state is still not formed. For this reason, the surgical instrument unit support body $1a$ and the intermediate member support body $2a$ are capable of further approaching each other. However, the input-side transmission shaft section $1A_X$ and the intermediate shaft $2b_X$ are in contact with each other in the axial direction. For this reason, while not shown, engagement between the connecting section $1B_X$ and the engaging protrusion $9c_X$ is deviated, and thus movement of the connecting section $1B_X$ and the input-side transmission shaft section $1A_X$ is stopped.

In addition, engagement between the connecting section $1B_Y$ and the engaging protrusion $9c_Y$ is not deviated. For this reason, the connecting section $1B_Y$ and the input-side transmission shaft section $1A_Y$ move further toward the distal end side, and as shown in FIG. 12A, the engaging protrusion $13a_Y$ is engaged with the concave engaging section $1f_Y$ (corresponding to a state of FIG. 7C).

When the surgical instrument unit 1 is further inserted into the surgical instrument unit insertion hole $2d$, as shown in FIG. 12B, the input-side transmission shaft section $1A_Y$ and the intermediate shaft $2b_Y$ are in contact with each other. For this reason, while not shown, engagement between the connecting section $1B_Y$ and the engaging protrusion $9c_Y$ is deviated, and movement of the connecting section $1B_Y$ and the input-side transmission shaft section $1A_Y$ is stopped.

As described above, the surgical instrument unit 1 is inserted into the surgical instrument unit insertion hole $2d$ until the surgical instrument unit support body $1a$ contacts the intermediate member support body $2a$ and does not move. At that time, each of the hook portions 16 comes into contact with the end portion of the intermediate member support body $2a$ (see FIG. 12A) to be pushed thereonto, and then, as shown in FIG. 12B, each of the engaging protrusions 16a is engaged with each of the concave engaging sections 2f.

As described above, the shaft engagement process and the support body engagement process are terminated.

Next, the attachment and detachment ring 9 is slid to a shaft engagement fixing position of the distal end side of the surgical instrument unit support body 1a in the axial direction, and as shown in FIG. 12C, the shaft engagement fixing process and the support body engagement fixing process are performed in parallel.

In the embodiment, the attachment and detachment ring 9 is installed at the outer circumferential portion of the surgical instrument unit support body 1a. For this reason, an operator slides the attachment and detachment ring 9 in the same direction as the moving direction of the surgical instrument unit 1 while holding the surgical instrument unit 1 in his or her hands, and this motion may be performed extremely easily and rapidly.

In addition, manipulation of the attachment and detachment ring 9 may be continuously performed from the insertion motion of the surgical instrument unit 1 into the intermediate member 2. For this reason, the mounting motion may be performed through a one-step operation. For example, from the beginning, when the surgical instrument unit 1 is inserted with holding the attachment and detachment ring 9, the surgical instrument unit 1 contacts the intermediate member 2 in the axial direction to automatically move only the attachment and detachment ring 9 in the axial direction. For this reason, there is no need for a two-step operation in which switching the surgical instrument unit 1 from one hand to another hand or put another hand on the surgical instrument unit 1 which held by one hand to move the attachment and detachment ring 9.

In addition, when the above-mentioned motions are performed in reverse, the shaft engagement fixing release process, the support body fixing release process, the shaft engagement release process, and the support body engagement release process may be performed.

While these motions can be easily understood from the above description, a motion of only the shaft attachment and detachment mechanism unit 11A will be described in brief.

Figure 13A:
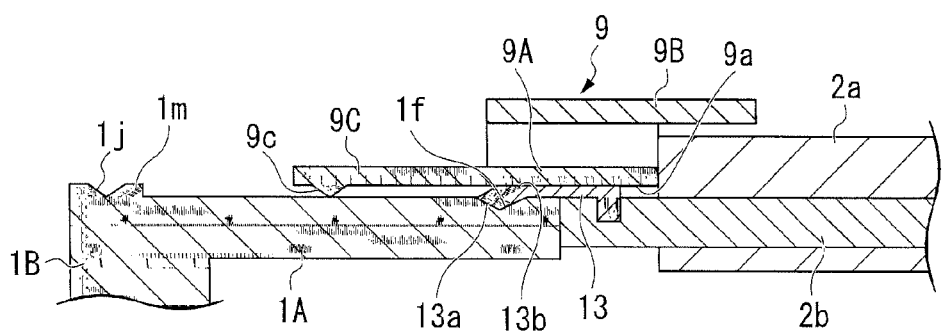
FIG. 13A is a view for schematically describing a motion in which the surgical instrument unit is dismounted from the intermediate member of the operation support device according to the first embodiment of the invention.
Figure 13B:
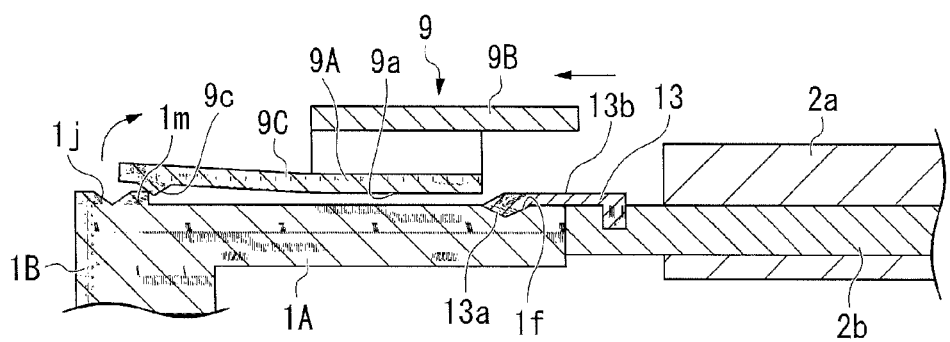
FIG. 13B is a view for schematically describing a motion in which the surgical instrument unit is dismounted from the intermediate member of the operation support device according to the first embodiment of the invention.
Figure 13C:
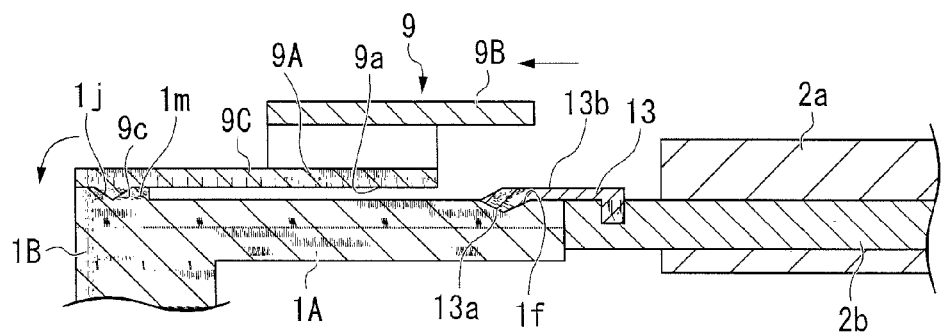
FIG. 13C is a view for schematically describing a motion in which the surgical instrument unit is dismounted from the intermediate member of the operation support device according to the first embodiment of the invention.

In order to release the shaft engagement fixing from the first state shown in FIG. 13A, the attachment and detachment ring 9 is slid to the proximal end side while holding the outer circumference ring section 9B (see FIG. 13B).

At this time, when the inner circumference pressing section 9A is moved to the proximal end side rather than the hook portion 13, holding down to the hook portion 13 is released. For this reason, the hook portion 13 is capable of being pivoted, and the shaft engagement fixing state is released.

Further, when the attachment and detachment ring 9 is moved to the proximal end side, as shown in FIG. 13B, the engaging protrusion 9c comes into contact with the step-shaped protrusion section 1m, the rod-shaped portion 9C is flexibly deformed, and the engaging protrusion 9c is pushed up onto the step-shaped protrusion section 1m. At this time, while the connecting section 1B is held down toward the proximal end side, since the engagement state between the hook portion 13 and the concave engaging section 1f is not released, the connecting section 1B and the input-side transmission shaft section 1A do not move.

When the engaging protrusion 9c is disposed on the concave engaging section 1j, the engaging protrusion 9c is engaged with the concave engaging section 1j. At this time, the engaging protrusion 9c is securely fitted into the concave engaging section 1f by an elastic recovering force of the rod-shaped portion 9C to be biased inward in the radial direction.

For this reason, the attachment and detachment ring 9 is integrated with the connecting section 1B to move the attachment and detachment ring 9 toward the proximal end side so that the manipulation is capable of being securely transmitted to the connecting section 1B. Therefore, the connecting section 1B and the input-side transmission shaft section 1A begin to move toward the proximal end side.

Figure 13D:
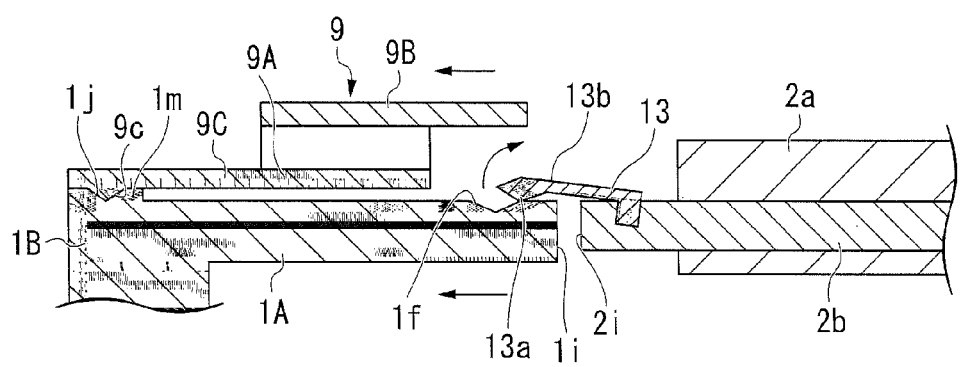
FIG. 13D is a view for schematically describing a motion in which the surgical instrument unit is dismounted from the intermediate member of the operation support device according to the first embodiment of the invention.

At this time, as shown in FIG. 13D, since the hook portion 13 is in a pivotable state, when the input-side transmission shaft section 1A begins to be pivoted clockwise shown in FIG. 13D, engagement with the concave engaging section 1f is released. Accordingly, the input-side transmission shaft section 1A is separated from the intermediate shaft 2b to space the distal end surface 1i and the proximal end surface 2i from each other.

As described above, the shaft engagement state is released, and the shaft engagement release process is terminated.

When the attachment and detachment ring 9 is moved to the released position, the attachment and detachment ring 9 is capable of moving only when the attachment and detachment ring 9 is moved with the surgical instrument unit support body 1a. For this reason, when the attachment and detachment ring 9 is moved to the proximal end side while the operator holds the attachment and detachment ring 9, the surgical instrument unit 1 is also automatically moved to the proximal end side and pulled up from the intermediate member 2.

As described above, the mounting release is terminated.

In the motion of releasing the mounting in the embodiment, since an external force for moving the connecting section 2A to the proximal end side is scarcely transmitted to the intermediate shaft 2b, the shaft engagement state is capable of being released with almost no resistance.

As described above, in the operation support device 50 according to the embodiment, the first support body and the second support body are moved in the moving direction of the first shaft section and the second shaft section, and thus engagement or engagement release between the first shaft section and the second shaft section may be performed. Further, the attachment and detachment may be performed through the simple manipulation in which the shaft engagement fixing state and the shaft engagement release state are selectively formed by moving the shaft fixing member. For this reason, the attachment and detachment of the surgical instrument unit with respect to the surgical instrument drive unit is capable of being easily and rapidly performed.

In addition, in the embodiment, the attachment and detachment motion is moved in the axial direction only. For this reason, upon the mounting, the surgical instrument unit 1 is inserted into the intermediate member 2 to complete the attachment and detachment. That is, the mounting may be performed by an extremely simple one-step manipulation.

Upon the attachment and detachment, even when protruding positions of the intermediate shafts 2b are different, if the attachment and detachment motion is performed, according to the positions of the intermediate shafts 2b, the positions of the input-side transmission shaft sections 1A follow the intermediate shafts 2b. For this reason, the attachment and detachment may be performed regardless of the positions of the intermediate shafts 2b.

Furthermore, even upon the mounting or the mounting release (upon separation), the attachment and detachment ring 9 may be operated in the same direction as the attachment and detachment direction while holding the outer circumferential surface of the surgical instrument unit 1 including the attachment and detachment ring 9. For this reason, the attachment and detachment manipulation may be simply performed, and the attachment and detachment manipulation becomes easy.

For this reason, when rapid separation of the surgical instrument unit 1 is particularly needed, the attachment and detachment may be securely performed.

In the description of the shaft engagement process with reference to FIG. 11A, FIG. 11B and FIG. 11C, it has been described that the mounting may be easily performed even when stoppage positions in the axial direction of the drive force transmission shafts 3b are different. Even when positions in the axial direction of the drive force transmission shafts 3b are different in the shaft engagement release process as described above, the surgical instrument unit 1 may be easily separated.

In addition, in the embodiment, the surgical instrument drive unit 3 is spaced apart from the surgical instrument unit 1 via the intermediate member 2 and the drape 7. For this reason, assembly of the surgical instrument unit 1 and the intermediate member 2 may be performed in the second region $A_C$ only. For this reason, exchange of the surgical instrument unit 1 during the surgery may be rapidly and easily performed.

Further, in the embodiment, the surgical instrument unit 1 is inserted into the intermediate member 2 and connected thereto. For this reason, for example, since the surgical instrument unit 1 is capable of being performed the attachment and detachment from the upside toward the connecting body of the intermediate member 2 and the surgical instrument drive unit 3, which supported by the arm over a patient, the attachment and detachment work may be efficiently performed.

Second Embodiment

Next, an operation support device according to a second embodiment of the invention will be described.

FIG. 14A, FIG. 14B, FIG. 14C and FIG. 14D are schematic configuration views and motion describing views of major parts of an attachment and detachment mechanism of the operation support device according to the second embodiment of the invention.

An operation support device 51 according to the embodiment includes a shaft attachment and detachment mechanism unit 21A, instead of the shaft attachment and detachment mechanism unit 11A of the operation support device 50 of the first embodiment shown in FIG. 2A.

Figure 14A:
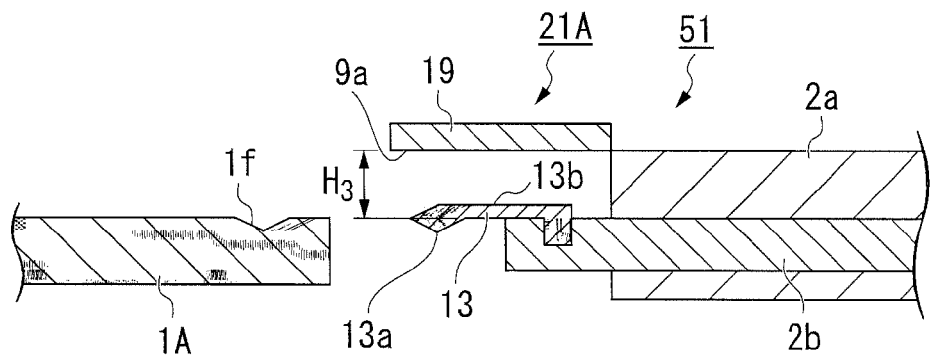
FIG. 14A is a schematic configuration view and a motion describing view of major parts of an attachment and detachment mechanism of an operation support device according to a second embodiment of the invention.
Figure 14B:
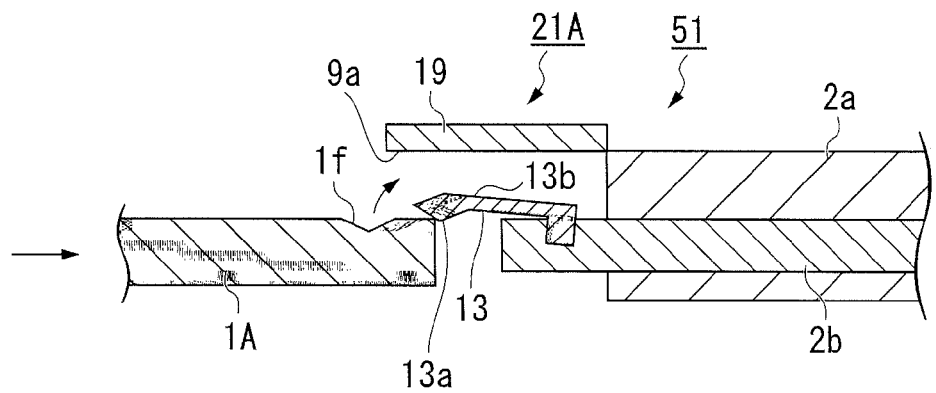
FIG. 14B is a schematic configuration view and a motion describing view of the major parts of the attachment and detachment mechanism of the operation support device according to the second embodiment of the invention.
Figure 14C:
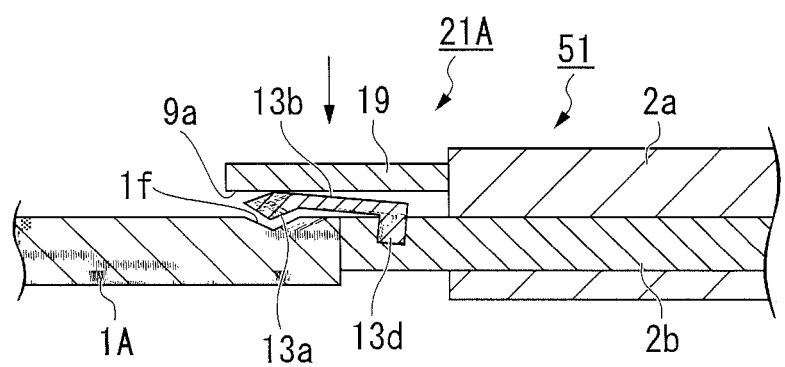
FIG. 14C is a schematic configuration view and a motion describing view of the major parts of the attachment and detachment mechanism of the operation support device according to the second embodiment of the invention.
Figure 14D:
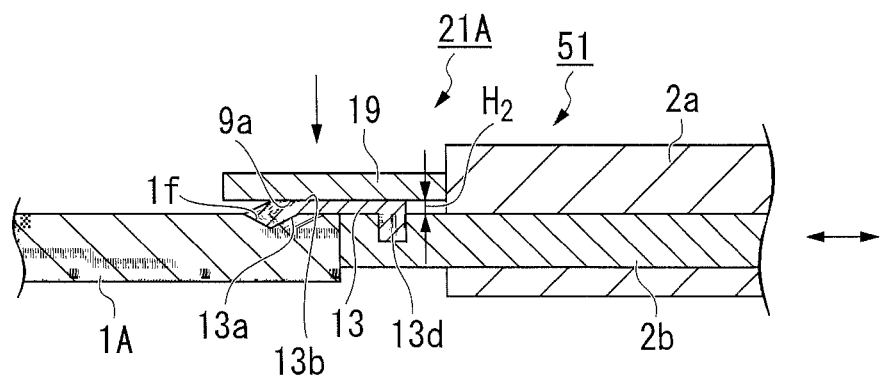
FIG. 14D is a schematic configuration view and a motion describing view of the major parts of the attachment and detachment mechanism of the operation support device according to the second embodiment of the invention.

As shown in FIG. 14A, the shaft attachment and detachment mechanism unit 21A includes a pressing member 19 (a shaft fixing member), instead of the inner circumference pressing section 9A of the shaft attachment and detachment mechanism unit 11A of the first embodiment. Hereinafter, the second embodiment will be described focusing on differences from the first embodiment.

The pressing member 19 is installed at the proximal end portion of the intermediate member support body 2a, and movably supported in the radial direction, which is a vertical direction shown in FIG. 14A, in a range outside in the radial direction more than the intermediate shaft 2b and the hook portion 13. In addition, as shown in FIG. 14A, the pressing member 19 is configured to enable selective movement between the shaft engagement release position and the shaft engagement fixing position by a manipulation member (not shown) and fixing of the positions after the movement. The shaft engagement release position is a position having the height $H_3$ (however, $H_3 > H_2$) at which the hook portion 13 is capable of being rotated. In addition, the shaft engagement fixing position is a position at which a height from the outer circumference side surface 2h becomes $h_2$.

The same position restricting surface 9a as in the first embodiment is formed inside in the radial direction of the pressing member 19.

As the manipulation member of the pressing member 19, for example, a push button protruding toward the outer circumferential portion of the intermediate member support body 2a, a slide member configured to slide on the outer circumferential portion of the intermediate member support body 2a in the axial direction, a rotary ring rotatably installed at the outer circumferential portion of the intermediate member support body 2a in the circumferential direction, and so on, may be employed. In addition, the manipulation member and the pressing member 19 may be connected to each other via a direction conversion mechanism for appropriately converting a direction of a manipulation force.

A motion of the operation support device 51 having the above-mentioned configuration will be described focusing on differences from the first embodiment.

In the embodiment, the input-side transmission shaft section 1A is relatively moved with respect to the intermediate shaft 2b, the engaging protrusion 13a of the hook portion 13 is engaged with the concave engaging section 1f, or a motion of releasing the engagement is similar to the first embodiment.

That is, as shown in FIG. 14A, in a state in which the pressing member 19 is disposed at the shaft engagement release position, the input-side transmission shaft section 1A approaches the intermediate shaft 2b. Accordingly, the hook portion 13 is pivoted (see FIG. 14B). Then, the engaging protrusion 13a is engaged with the concave engaging section 1f (see FIG. 14C).

After the engaging protrusion 13a is engaged with the concave engaging section 1f, the manipulation member (not shown) is operated, and the pressing member 19 is moved to the shaft engagement fixing position to be fixed to a position in the radial direction of the pressing member 19. Accordingly, since the hook portion 13 is sandwiched between the outer circumference side surfaces 1h and 2h and the position restricting surface 9a, the first state is formed similar to the first embodiment. Accordingly, the shaft engagement fixing process according to the embodiment is terminated.

By performing these motions in reverse, the shaft engagement fixing release process and the shaft engagement release process may be performed.

According to the operation support device 51 according to the embodiment, in a state in which the surgical instrument unit 1 is inserted into the intermediate member 2 and then the surgical instrument unit 1 is held by operation of the manipulation member installed at the outer circumferential portion of the intermediate member 2, the shaft engagement fixing process and the shaft engagement fixing release process may be performed. For this reason, the attachment and detachment manipulation of the surgical instrument unit 1 may be rapidly and easily performed.

The embodiment is an example in the case in which the first shaft engaging section is installed at the second shaft section, the shaft connecting member is installed at the first shaft section, and the shaft fixing member advances and retreats in the radial direction. In this example, the radial direction is a direction crossing the axial direction which functions as the moving direction and the attachment and detachment direction of the first shaft section and the second shaft section.

Third Embodiment

Next, an operation support device according to a third embodiment of the invention will be described.

Figure 15A:
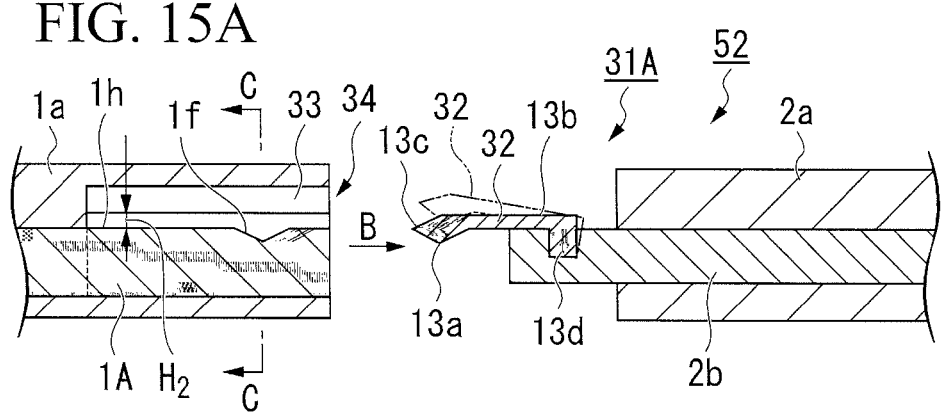
FIG. 15A is a schematic configuration view of major parts of an attachment and detachment mechanism of an operation support device according to a third embodiment of the invention.
Figure 15B:
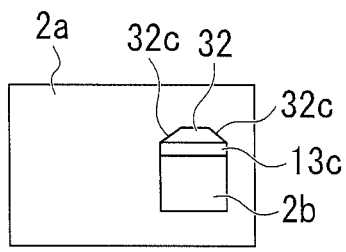
FIG. 15B is a view when seen from an arrow B of FIG. 15A.
Figure 15C:
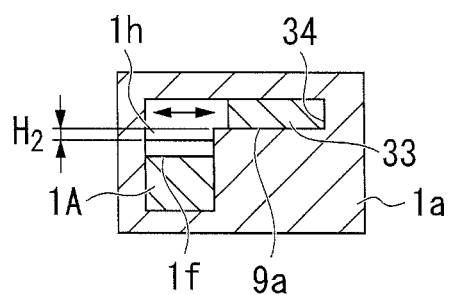
FIG. 15C is a cross-sectional view taken along line C-C of FIG. 15A.

FIG. 15A is a schematic configuration view of major parts of an attachment and detachment mechanism of the operation support device according to the third embodiment of the invention. FIG. 15B is a view when seen in a direction of an arrow B of FIG. 15A. FIG. 15C is a cross-sectional view taken along line C-C of FIG. 15A. FIG. 16A, FIG. 16B, FIG. 16C and FIG. 16D are views for schematically describing a motion of the attachment and detachment mechanism of the operation support device according to the third embodiment of the invention.

An operation support device 52 according to the embodiment includes a shaft attachment and detachment mechanism unit 31A, instead of the shaft attachment and detachment mechanism unit 11A of the operation support device 50 of the first embodiment shown in FIG. 2A.

As shown in FIG. 15A, the shaft attachment and detachment mechanism unit 31A is a member including a pressing member 33 (a shaft fixing member) and a hook portion 32 (a shaft connecting member), instead of the inner circumference pressing section 9A of the shaft attachment and detachment mechanism unit 11A and the hook portion 13 according to the first embodiment, and further including a pressing member guide groove 34. Hereinafter, the third embodiment will be described focusing on differences from the first embodiment.

The pressing member 33 is a plate-shaped member installed to enable advance or retreat at a position that becomes the outside (an upper side of FIG. 15A) in the radial direction of the distal end portion of the input-side transmission shaft section 1A in the distal end portion of the surgical instrument unit support body 1a. The pressing member 33 has a position restricting surface 9a formed inside in the radial direction.

In addition, as shown in FIG. 15C, the pressing member 33 is put in the pressing member guide groove 34. The pressing member guide groove 34 holds the position restricting surface 9a at a position of the height $H_2$ from the outer circumference side surface 1h.

As shown in FIG. 15C, at the position where the pressing member 33 is retreat in the pressing member guide groove 34, an upper side of the concave engaging section 1f is not covered by the pressing member 33. For this reason, the shaft engagement fixing is in a released state. This position is referred to as a shaft engagement fixing release position. In addition, as shown in FIG. 16D, at a position where the pressing member 33 moves toward the upper side of the input-side transmission shaft section 1A and the position restricting surface 9a opposes the outer circumference side surface 1h, a fixing state of the shaft engagement is formed. This position is referred to as a shaft engagement fixing position.

Further, the pressing member 33 is connected to the manipulation member (not shown), and thus, the advance/retreat position of the pressing member 33 is capable of being selectively operated.

As the manipulation member of the pressing member 33, for example, a member having the same configuration as the second embodiment may be formed at the outer circumferential portion of the surgical instrument unit support body 1a. In addition, the manipulation member and the pressing member 33 may be connected to each other via the same direction conversion mechanism as in the second embodiment.

The hook portion 32 has both ends chamfered in a width direction (a leftward/rightward direction of FIG. 15B) of the outer circumferential surface 13b of the hook portion 13 according to the first embodiment, and thus a taper 32c is formed to extend in a longitudinal direction (a leftward/rightward direction of FIG. 15A).

A motion of the operation support device 52 having the above-mentioned configuration will be described focusing differences from the first embodiment.

In the embodiment, the input-side transmission shaft section 1A is relatively moved with respect to the intermediate shaft 2b, the engaging protrusion 13a of the hook portion 32 is engaged with the concave engaging section 1f, or the engagement release motion is similar to the above-mentioned embodiment.

Figure 16A:
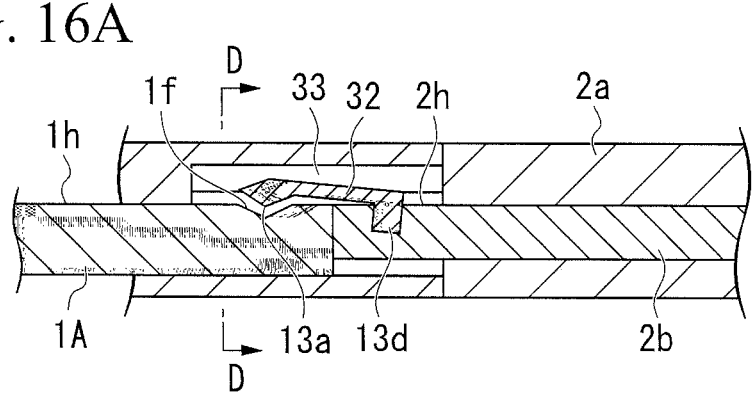
FIG. 16A is a view for schematically describing a motion of the attachment and detachment mechanism of the operation support device according to the third embodiment of the invention.
Figure 16B:
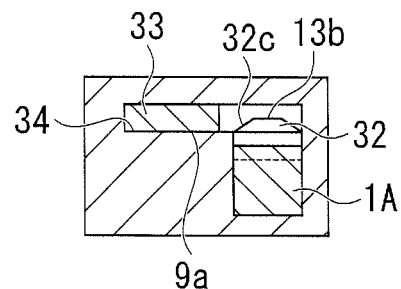
FIG. 16B is a view for schematically describing a motion of the attachment and detachment mechanism of the operation support device according to the third embodiment of the invention.

That is, the input-side transmission shaft section 1A and the intermediate shaft 2b move relative to each other as shown in FIG. 16B from a state shown in FIG. 15A, and the engaging protrusion 13a of the hook portion 32 is engaged with the concave engaging section 1f. Until the engaging protrusion 13a is engaged with the concave engaging section 1f, the pressing member 33 is retreat to the shaft engagement fixing release position.

Figure 16C:
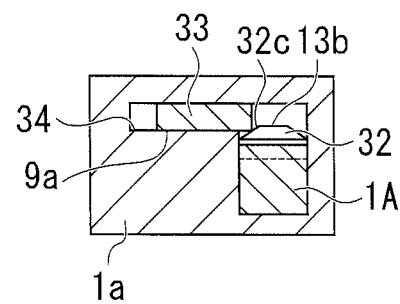
FIG. 16C is a view for schematically describing a motion of the attachment and detachment mechanism of the operation support device according to the third embodiment of the invention.
Figure 16D:
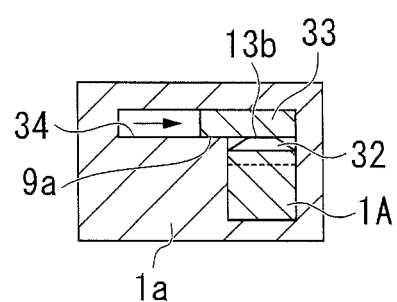
FIG. 16D is a view for schematically describing a motion of the attachment and detachment mechanism of the operation support device according to the third embodiment of the invention.

The manipulation member (not shown) is operated from this state and the pressing member 33 moves forward to the shaft engagement fixing position. At this time, as shown in FIG. 16C, even when the hook portion 32 is raised from the outer circumference side surfaces 1h and 2h, as the pressing member 33 comes into contact with the taper 32c, the hook portion 32 is held down toward the outer circumference side surfaces 1h and 2h.

Figure 16E:
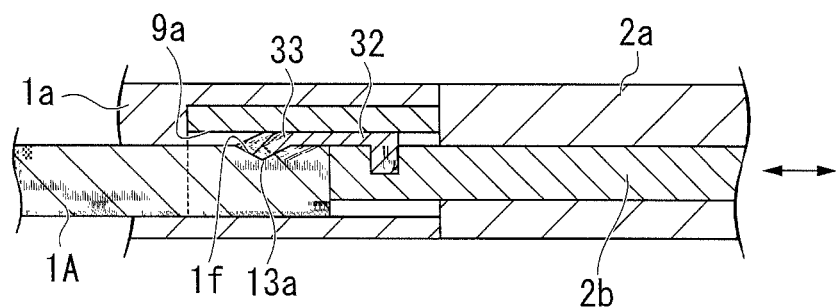
FIG. 16E is a view for schematically describing a motion of the attachment and detachment mechanism of the operation support device according to the third embodiment of the invention.

Accordingly, as shown in FIG. 16D and FIG. 16E, when the pressing member 33 is moved to the shaft engagement fixing position, the hook portion 32 is sandwiched between the outer circumference side surfaces 1h and 2h and the position restricting surface 9a. For this reason, the same first state as in the first embodiment may be formed. Accordingly, the shaft engagement fixing process is terminated.

By performing these motions in reverse, the shaft engagement fixing release process and the shaft engagement release process may be performed.

According to the operation support device 52 of the embodiment, by operation of the manipulation member at the outer circumferential surface of the surgical instrument unit 1, the shaft engagement fixing process and the shaft engagement fixing release process may be performed in a state in which the surgical instrument unit 1 is held. For this reason, operation for attaching and detaching the surgical instrument unit 1 may be rapidly and easily performed.

The embodiment is an example of the case in which the first shaft engaging section is installed at the second shaft section, the shaft connecting member is installed at the first shaft section, and the shaft fixing member advances or retreats in the circumferential direction. In this example, the circumferential direction crosses the axial direction which functions as the moving direction and the attachment and detachment direction of the first shaft section and the second shaft section.

Fourth Embodiment

Next, an operation support device according to a fourth embodiment of the invention will be described.

FIG. 17A, FIG. 17B, FIG. 17C and FIG. 17D are schematic configuration views and motion describing views of major parts of an attachment and detachment mechanism of the operation support device according to the fourth embodiment of the invention.

An operation support device 53 according to the embodiment includes a shaft attachment and detachment mechanism unit 41A, instead of the shaft attachment and detachment mechanism unit 11A of the operation support device 50 according to the first embodiment shown in FIG. 2A.

Figure 17A:
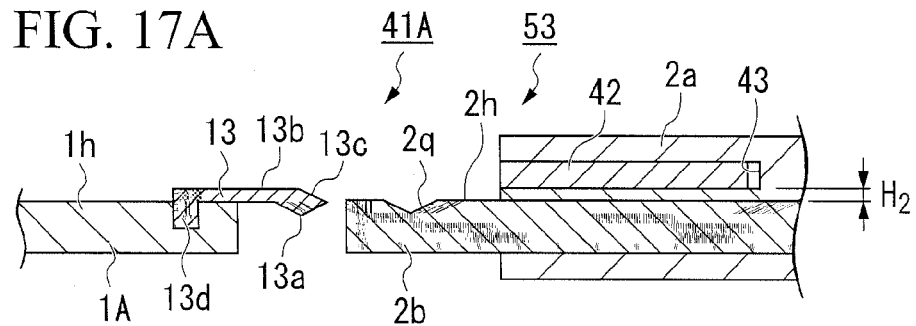
FIG. 17A is a schematic configuration view and a motion describing view of major parts of an attachment and detachment mechanism of an operation support device according to a fourth embodiment of the invention.
Figure 17B:
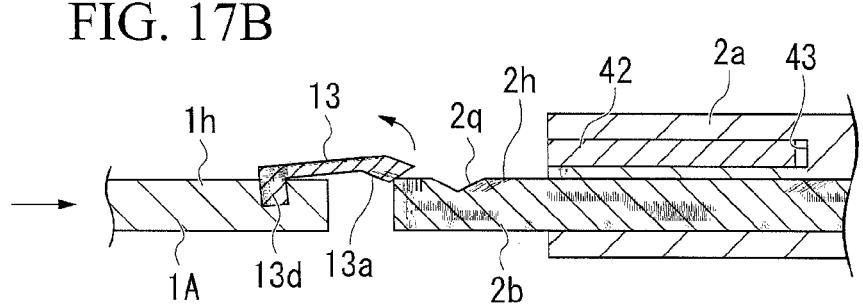
FIG. 17B is a schematic configuration view and a motion describing view of the major parts of the attachment and detachment mechanism of the operation support device according to the fourth embodiment of the invention.
Figure 17C:
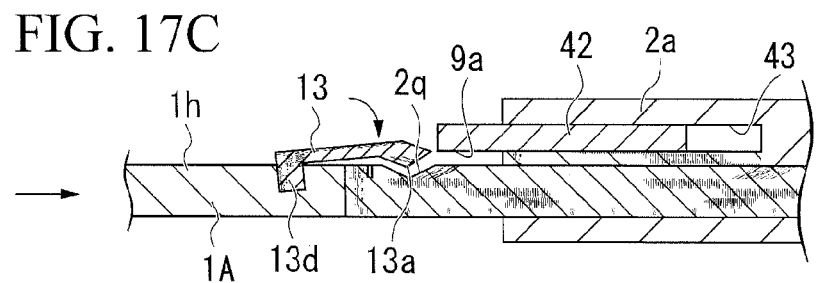
FIG. 17C is a schematic configuration view and a motion describing view of the major parts of the attachment and detachment mechanism of the operation support device according to the fourth embodiment of the invention.

As shown in FIG. 17A, the shaft attachment and detachment mechanism unit 41A includes a pressing member 42 (a shaft fixing member), instead of the inner circumference pressing section 9A of the shaft attachment and detachment mechanism unit 11A according to the first embodiment. Thus, the shaft attachment and detachment mechanism unit 41A is an example including a pressing member guide groove 43 and a concave engaging section 2q (a shaft engaging section) without forming the concave engaging section 1f according to the first embodiment.

However, in the embodiment, the hook portion 13 is formed at the distal end portion of the input-side transmission shaft section 1A. Hereinafter, the fourth embodiment will be described focusing on differences from the first embodiment.

The pressing member 42 is a plate-shaped member installed to enable advance and retreat in the axial direction (a leftward and rightward direction of FIG. 17A) in the distal end portion of the intermediate member support body 2a. The position restricting surface 9a is formed inside in the radial direction (a lower side of FIG. 17A).

In addition, the pressing member 42 is put in the pressing member guide groove 43 configured to hold the position restricting surface 9a at a position of the height $H_2$ from the outer circumference side surface 1h.

Figure 17D:
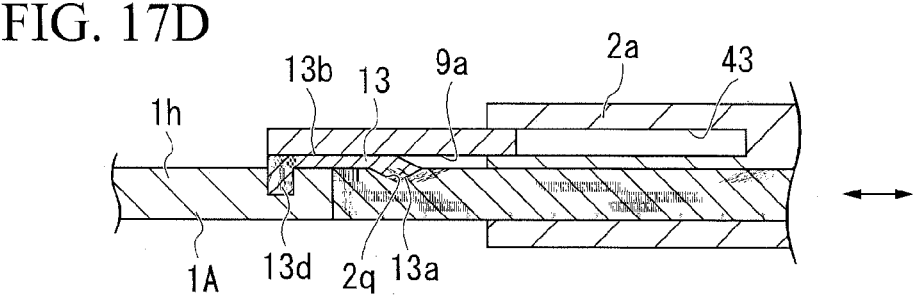
FIG. 17D is a schematic configuration view and a motion describing view of the major parts of the attachment and detachment mechanism of the operation support device according to the fourth embodiment of the invention.

As shown in FIG. 15A, in a state in which the pressing member 42 is retreat in the pressing member guide groove 43, the intermediate shaft 2b is not covered by the pressing member 42. For this reason, a state in which the shaft is released from the engagement fixing state is formed. This position is referred to as a shaft engagement fixing release position. In addition, as shown in FIG. 17D, the pressing member 42 moves forward to the proximal end side in the axial direction to form a state in which the engagement of the shaft is fixed at a position at which the position restricting surface 9a covers the hook portion 13 formed at the distal end portion of the intermediate shaft 2b and the input-side transmission shaft section 1A. This position is referred to as a shaft engagement fixing position.

Further, the pressing member 42 is connected to the manipulation member (not shown), and is configured to construct an advance and retreat position of the pressing member 42 which is capable of being selectively manipulated.

As the manipulation member of the pressing member 42, for example, the same configuration as in the second embodiment is capable of being installed at the outer circumferential portion of the intermediate member support body 2a. In addition, the manipulation member and the pressing member 42 may be connected to each other via the same direction conversion mechanism as in the second embodiment.

The concave engaging section 2q is configured such that the concave engaging section 1f according to the first embodiment is installed on the outer circumference side surface 2h of the intermediate shaft 2b. A relative positional relationship between the hook portion 13 and the concave engaging section 2q formed at the input-side transmission shaft section 1A is similar to the relationship between the hook portion 13 and the concave engaging section 1f according to the first embodiment, except that the installed members are reversed.

A motion of the operation support device 53 having the above-mentioned configuration will be described focusing on differences from the first embodiment.

In the embodiment, a motion in which the input-side transmission shaft section 1A is relatively moved with respect to the intermediate shaft 2b and the engaging protrusion 13a of the hook portion 13 is engaged with the concave engaging section 2q or the engagement is released is similar to that in the first embodiment.

That is, as shown in FIG. 17A, in a state in which the pressing member 42 is disposed at the shaft engagement fixing release position, the input-side transmission shaft section 1A approaches the intermediate shaft 2b. Accordingly, the hook portion 13 is pivoted (see FIG. 17B) to be engaged with the concave engaging section 2q (see FIG. 17C)

After the engaging protrusion 13a is engaged with the concave engaging section 2q, the manipulation member (not shown) is operated, the pressing member 42 is moved to the shaft engagement fixing position, and a position in the axial direction of the pressing member 42 is fixed. Accordingly, since the hook portion 13 is sandwiched between the outer circumference side surfaces 1h and 2h and the position restricting surface 9a, the same first state as in the first embodiment may be formed. As described above, the shaft engagement fixing process according to the embodiment is terminated.

By performing these motions in reverse, the shaft engagement fixing release process and the shaft engagement release process may be performed.

According to the operation support device 53 according to the embodiment, after the surgical instrument unit 1 is inserted into the intermediate member 2, by operation of the manipulation member installed at the outer circumferential portion of the intermediate member 2, the shaft engagement fixing process and the shaft engagement fixing release process may be performed in a state in which the surgical instrument unit 1 is held. For this reason, the attachment and detachment manipulation of the surgical instrument unit 1 may be rapidly and easily performed.

The embodiment is an example in the case in which the first shaft engaging section is installed at the first shaft section, the shaft connecting member is installed at the second shaft section, and the shaft fixing member advances and retreats in the axial direction from the first support body side to the second support body side. In this example, the axial direction functions as the moving direction and the attachment and detachment direction of the first shaft section and the second shaft section.

Fifth Embodiment

Next, an operation support device according to a fifth embodiment of the invention will be described.

FIG. 18A, FIG. 8B, FIG. 18C and FIG. 18D are schematic configuration views for describing motions of major parts of an attachment and detachment mechanism of the operation support device according to the fifth embodiment of the invention.

An operation support device 54 according to the embodiment includes a shaft attachment and detachment mechanism unit 61A, instead of the shaft attachment and detachment mechanism unit 11A of the operation support device 50 according to the first embodiment shown in FIG. 2A.

Figure 18A:
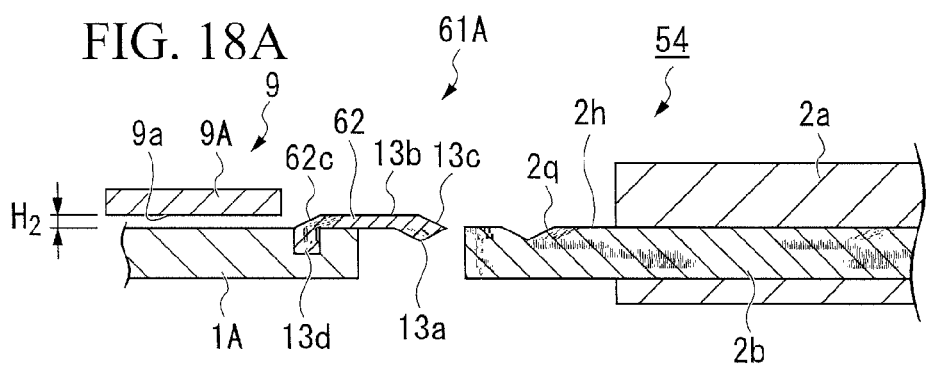
FIG. 18A is a view for schematically describing a motion of major parts of an attachment and detachment mechanism of an operation support device according to a fifth embodiment of the invention.

As shown in FIG. 18A, the shaft attachment and detachment mechanism unit 61A includes a hook portion 62 (a shaft connecting member), instead of the hook portion 13 of the shaft attachment and detachment mechanism unit 11A according to the first embodiment, and further includes the concave engaging section 2q (the shaft engaging section) according to the fourth embodiment, while the concave engaging section 1f is not formed. Hereinafter, the fifth embodiment will be described focusing on differences from the first and fourth embodiments.

The hook portion 62 is configured to form a taper 62c at an end portion of the hinge portion 13d side of the outer circumferential surface 13b of the hook portion 13 according to the first embodiment. However, the hook portion 62 is formed at the distal end portion of the input-side transmission shaft section 1A, similar to the hook portion 13 according to the fourth embodiment.

For this reason, the hook portion 62 and the concave engaging section 2q according to the embodiment are formed to have the same positional relationship as the positional relationship between the hook portion 13 and the concave engaging section 2q according to the fourth embodiment.

A motion of the operation support device 53 having the above-mentioned configuration will be described focusing on differences from the first embodiment.

Figure 18B:
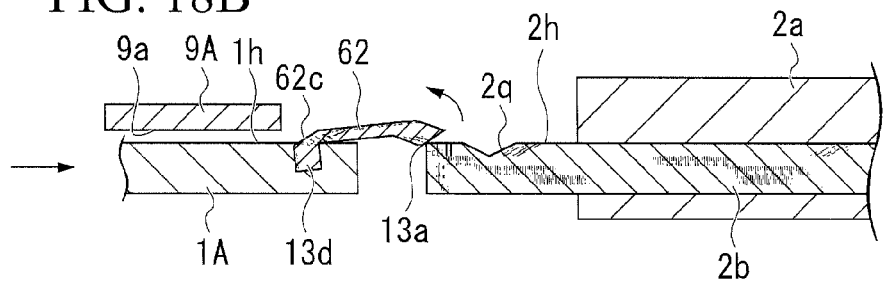
FIG. 18B is a view for schematically describing a motion of the major parts of the attachment and detachment mechanism of the operation support device according to the fifth embodiment of the invention.

In the embodiment, a motion in which the input-side transmission shaft section 1A is relatively moved with respect to the intermediate shaft 2b and the engaging protrusion 13a of the hook portion 62 is engaged with the concave engaging section 2q or the engagement is released is similar to that according to the fourth embodiment (see FIG. 18A and FIG. 18B).

Figure 18C:
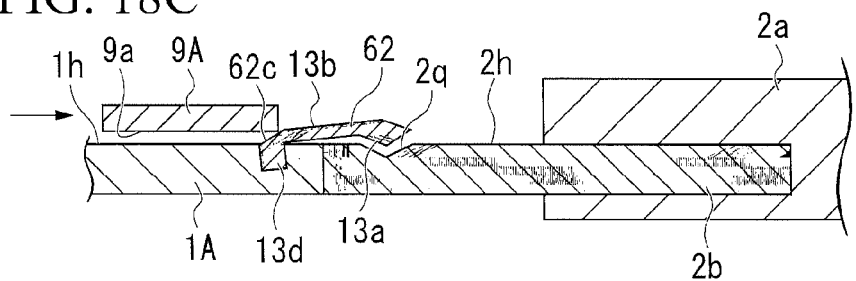
FIG. 18C is a view for schematically describing a motion of the major parts of the attachment and detachment mechanism of the operation support device according to the fifth embodiment of the invention.
Figure 18D:
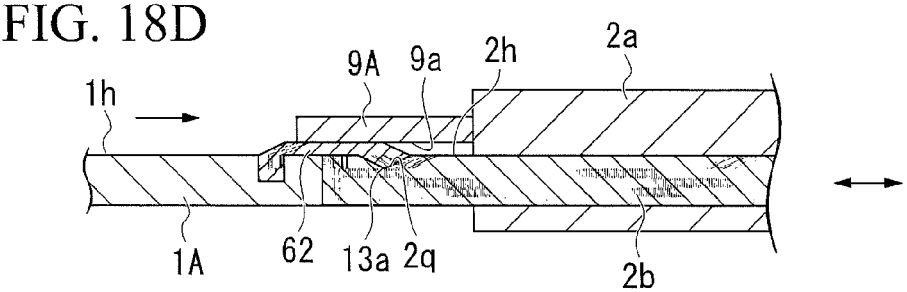
FIG. 18D is a view for schematically describing a motion of the major parts of the attachment and detachment mechanism of the operation support device according to the fifth embodiment of the invention.

However, in the embodiment, as shown in FIG. 18C and FIG. 18D, the difference is that the inner circumference pressing section 9A holds down the hook portion 62 from the end portion opposite to the taper 13c.

The hook portion 62 includes the taper 62c opposite to the taper 13c. For this reason, as shown in FIG. 18C, when the inner circumference pressing section 9A is moved to the distal end side, even when the hook portion 62 is engaged with the concave engaging section 2q without support from the outer circumference side surface 1h and the outer circumference side surface 2h, the distal end portion of the inner circumference pressing section 9A is smoothly pushed onto the taper 62c so that the hook portion 13 is capable of being held down downward to the outer circumference side surfaces 1h and 2h. For this reason, a state in which the shaft engagement is fixed as shown in FIG. 18D may be easily and securely formed.

As described above, according to the operation support device 54 according to the embodiment, similar to the first embodiment, by the attachment and detachment ring 9 being moved in the axial direction, the shaft engagement fixing process and the shaft engagement fixing release process may be performed while holding the surgical instrument unit 1. For this reason, the attachment and detachment operation of the surgical instrument unit 1 may be rapidly and easily performed.

The embodiment is an example of the case in which the first shaft engaging section is installed at first shaft section, the shaft connecting member is installed at the second shaft section, and the shaft fixing member advances and retreats in the axial direction from the second support body side to the first support body side. In this example, the axial direction functions as the moving direction and the attachment and detachment direction of the first shaft section and the second shaft section.

In addition, in the descriptions of the embodiments and modified examples, the example of the case in which an engagement structure is constituted by a concavo-convex portion having the shaft engaging section (the support body engaging section) formed of a concave portion and the connection engaging section (the support body connection engaging section) formed of a convex portion has been described. Further, for example, the engagement structure may be constituted by a concavo-convex portion having the shaft engaging section (the support body engaging section) formed of a convex portion and the connection engaging section (the support body connection engaging section) formed of a concave.

In the descriptions of the embodiments and modified examples, the example of the case in which the first state or the third state sandwiched between the flat surface of the outer circumference side surface or the outer circumferential surface of the shaft section (the support body) at which the shaft connecting member (the support body connecting member) is installed and the shaft fixing member (the support body fixing member) with almost no gap has been described. Further, for example, when necessary engagement strength is obtained, a gap in which the hook portion is movable may be formed between the shaft connecting member (the support body connecting member) and the shaft fixing member (the support body fixing member).

In addition, in the descriptions of the respective embodiments and modified examples, the example of the case in which the shaft fixing member (the support body fixing member) and the shaft connecting member (the support body connecting member) held down by the shaft fixing member (the support body fixing member) are in contact with flat surfaces (for example, the position restricting surface 9a and the outer circumferential surface 13b, or the like) has been described. A surface on which the shaft fixing member (the support body fixing member) and the shaft connecting member (the support body connecting member) are in contact with each other is not limited to the flat surfaces. For example, a curved surface such as a cylindrical surface having an axis in the moving direction may be provided, or a concavo-convex portion may be formed at one surface to be in line or point contact with each other in order to reduce sliding friction.

In addition, in the descriptions of the respective embodiments and modified examples, the example of the case in which the shaft connecting member (the support body connecting member) is installed at the shaft section (the support body) via the hinge portion has been described. Further, for example, similar to the rod-shaped portion 9C of the attachment and detachment ring 9, a substantially pivotable structure may be provided with a snap fitting structure such as a flexibly deformable shaft-shaped portion integrated with the shaft section (the support body).

In addition, in the descriptions of the embodiments and modified examples, the example of the case in which the cylindrical portion 1d of the surgical instrument unit 1 is inserted into the surgical instrument unit insertion hole 2d of the intermediate member 2, and the intermediate member 2 and the surgical instrument drive unit 3 are disposed at the intermediate section in the axial direction of the surgical instrument unit 1 has been described. Further, for example, the surgical instrument unit 1, the intermediate member 2 and the surgical instrument drive unit 3 may be serially connected in a sequence from the distal end side in the axial direction.

In addition, in any connection structure, a configuration constituted by the surgical instrument unit 1 and the surgical instrument drive unit 3 may be employed, without installing the intermediate member 2.

Further, in the description of the first embodiment, the example in the case in which the attachment and detachment motions by the shaft attachment and detachment mechanism unit 11A and the support body attachment and detachment mechanism unit 11B are performed in parallel by the attachment and detachment ring 9 has been described. Furthermore, the inner circumference pressing sections 9A and 9E may be constituted by separate members, and the attachment and detachment of the shaft section and the attachment and detachment of the support body may be separately performed.

In addition, in the description of the first embodiment, the example in the case in which the support body attachment and detachment mechanism unit 11B is provided in addition to the shaft attachment and detachment mechanism unit 11A has been described. However, since the attachment and detachment of the support bodies are easy in comparison with the case in which the shaft section and the support body having different stopping positions are connected, the support body attachment and detachment mechanism unit of the related art may be used instead of the support body attachment and detachment mechanism unit 11B.

Further, all of the elements described in the embodiments and modified examples may be performed through replacement of appropriate assembly or omission without departing from the technical idea of the invention.

For example, the shaft attachment and detachment mechanism unit 11A may be modified and each configuration of the shaft attachment and detachment mechanism unit 21A, 31A, 41A and 61A may be modified to be applied to the support body attachment and detachment mechanism unit 11B.

In addition, in the embodiments and modified examples, while the example in the case in which the first support body is the intermediate member 2 and the second support is the surgical instrument unit 1 has been described, the first support body may be the surgical instrument drive unit 3, and the second support body may be the intermediate member 2. That is, all the configurations of the shaft attachment and detachment mechanism unit 11A and the support body attachment and detachment mechanism unit 11B and configurations appropriately modified from these may be employed in the shaft attachment and detachment mechanism unit 12A and the support body attachment and detachment mechanism unit 12B.

Further, in the embodiments and modified examples, the surgical instrument drive unit support body 3a of the surgical instrument drive unit 3 may be provided as the first support body instead of the intermediate member support body 2a of the intermediate member 2, and a configuration such as the shaft attachment and detachment mechanism unit 11A and the support body attachment and detachment mechanism unit 11B may be installed between the surgical instrument drive unit 3 and the surgical instrument unit 1 without installing the intermediate member 2.

While preferred embodiments of the present invention have been described and illustrated above, it should be understood that these are exemplary of the present invention and are not to be considered as limiting. Additions, omissions, substitutions, and other modifications can be made without departing from the spirit or scope of the present invention. Accordingly, the present invention is not to be considered as being limited by the foregoing description, and is only limited by the scope of the appended claims.

What is claimed is:

1. An operation support device comprising:
    an intermediate member having:
        a connecting section installed at a proximal end of the intermediate member;
        a first cylindrical portion connecting to the connecting section and extended toward a distal side; and
        a first insertion hole extending through the connecting section and the first cylindrical portion in a longitudinal axial direction;
    a surgical instrument unit having:
        a surgical instrument unit support body installed at a proximal end of the surgical instrument unit;
        a second cylindrical portion having an operation unit installed at a distal end of the second cylindrical portion to connect the surgical instrument unit support body at a proximal end of the second cylindrical portion;
    a surgical instrument drive unit having:
        a surgical instrument drive unit support body; and
        a second insertion hole extending through the surgical instrument drive unit support body in the longitudinal axial direction,
    wherein the first cylindrical portion is inserted into the second insertion hole to connect the surgical instrument drive unit to the intermediate member,
    the second cylindrical portion is inserted into the first insertion hole to connect the surgical instrument unit to the intermediate member,
    the intermediate member has a first shaft section which advances and retracts in the longitudinal axial direction to transmit driving forces;
    the surgical instrument unit has a second shaft section which advances and retracts in the longitudinal axial direction to transmit driving forces to the operation unit;
    the surgical instrument drive unit has a third shaft section which advances and retracts in the longitudinal axial direction to transmit driving forces generated by a motor; and
    the surgical instrument drive unit is connected with the intermediate member to connect the third shaft section with the first shaft section, and the intermediate member is connected with the surgical instrument unit to connect the first shaft section with the second shaft section, thereby the driving force generated by the motor transmits to the operation unit.

2. The operation support device according to claim 1, further comprising first and second members for affixing a drape, the first and second members being configured relative to the surgical instrument drive unit to isolate the surgical instrument drive unit inside the drape while exposing the surgical instrument unit and the intermediate member outside the drape.

3. The operation support device according to claim 1,
    wherein a length of the first insertion hole is shorter than a length of the second cylindrical portion in the longitudinal axial direction, and
    a length of the second insertion hole is shorted than a length of the first cylindrical portion in the longitudinal axial direction.

4. The operation support device according to claim 1,
    wherein the second shaft section has a first shaft engaging section, the first shaft section has a shaft connecting member engaging with the first shaft engaging section, and the first shaft section and the second shaft section are connected so as to transmit the driving force by engaging the shaft connecting member with the first shaft engaging section in accordance with a connection between the intermediate member and the surgical instrument unit.

5. The operation support device according to claim 4, further comprising a shaft fixing member, wherein when the shaft connecting member is engaged with the first shaft engaging member, the shaft fixing member is configured to maintain an engagement of the shaft connecting member and the first shaft engaging member.

6. The operation support device according to claim 4, further comprising a support body fixing member, wherein the intermediate member has a support body engaging section, the surgical instrument unit has a support body connecting member engaging with the support body engaging section, and wherein when the support body connecting member is engaged with the support body engaging section, the support body fixing member is configured to maintain an engagement of the support body connecting member and support body engaging section.

* * * * *